US012564323B2

(12) United States Patent
Myers et al.

(10) Patent No.: US 12,564,323 B2
(45) Date of Patent: Mar. 3, 2026

(54) IMAGING APPARATUS WITH MULTIPLE STEREOSCOPIC CAMERAS

(71) Applicant: Alcon Inc., Fribourg (CH)

(72) Inventors: Gillian Myers, Santa Barbara, CA (US); Eric Aspnes, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 692 days.

(21) Appl. No.: 18/045,002

(22) Filed: Oct. 7, 2022

(65) Prior Publication Data

US 2023/0141727 A1 May 11, 2023

Related U.S. Application Data

(60) Provisional application No. 63/277,369, filed on Nov. 9, 2021.

(51) Int. Cl.
*A61B 3/14* (2006.01)
*A61B 3/00* (2006.01)

(52) U.S. Cl.
CPC ............ *A61B 3/145* (2013.01); *A61B 3/0058* (2013.01)

(58) Field of Classification Search
CPC ....... A61B 3/145; A61B 3/0058; A61B 90/30; A61B 2090/3616; A61B 2090/371; A61B 3/132; A61B 90/20; A61B 90/361
See application file for complete search history.

(56) References Cited

U.S. PATENT DOCUMENTS

| | | | |
|---|---|---|---|
| 6,473,229 B2 | 10/2002 | Nakamura | |
| 7,784,946 B2 * | 8/2010 | LeBlanc ................ | A61B 3/132 |
| | | | 351/221 |
| 10,426,339 B2 * | 10/2019 | Papac ................... | G06F 3/0416 |
| 11,058,513 B2 * | 7/2021 | Ramirez Luna ..... | H04N 13/239 |

FOREIGN PATENT DOCUMENTS

EP        0398118 A2    11/1990

* cited by examiner

*Primary Examiner* — Bumsuk Won
*Assistant Examiner* — Ray Alexander Dean

(57) ABSTRACT

This disclosure provides techniques and apparatuses for displaying stereoscopic video data associated with different viewing angles of a target surgical site. An example ophthalmic imaging apparatus includes a first camera head mounted in a first orbital position above a target surgical site associated with an eye of a patient, wherein the first camera head includes at least one stereoscopic lens set providing a first viewing angle of the target surgical site. Additionally, the ophthalmic imaging apparatus includes at least a second camera head mounted in a second orbital position above the target surgical site, wherein the second camera head includes at least one additional stereoscopic lens set providing a second viewing angle of the target surgical site different from the first viewing angle of the target surgical site.

15 Claims, 12 Drawing Sheets

600

900

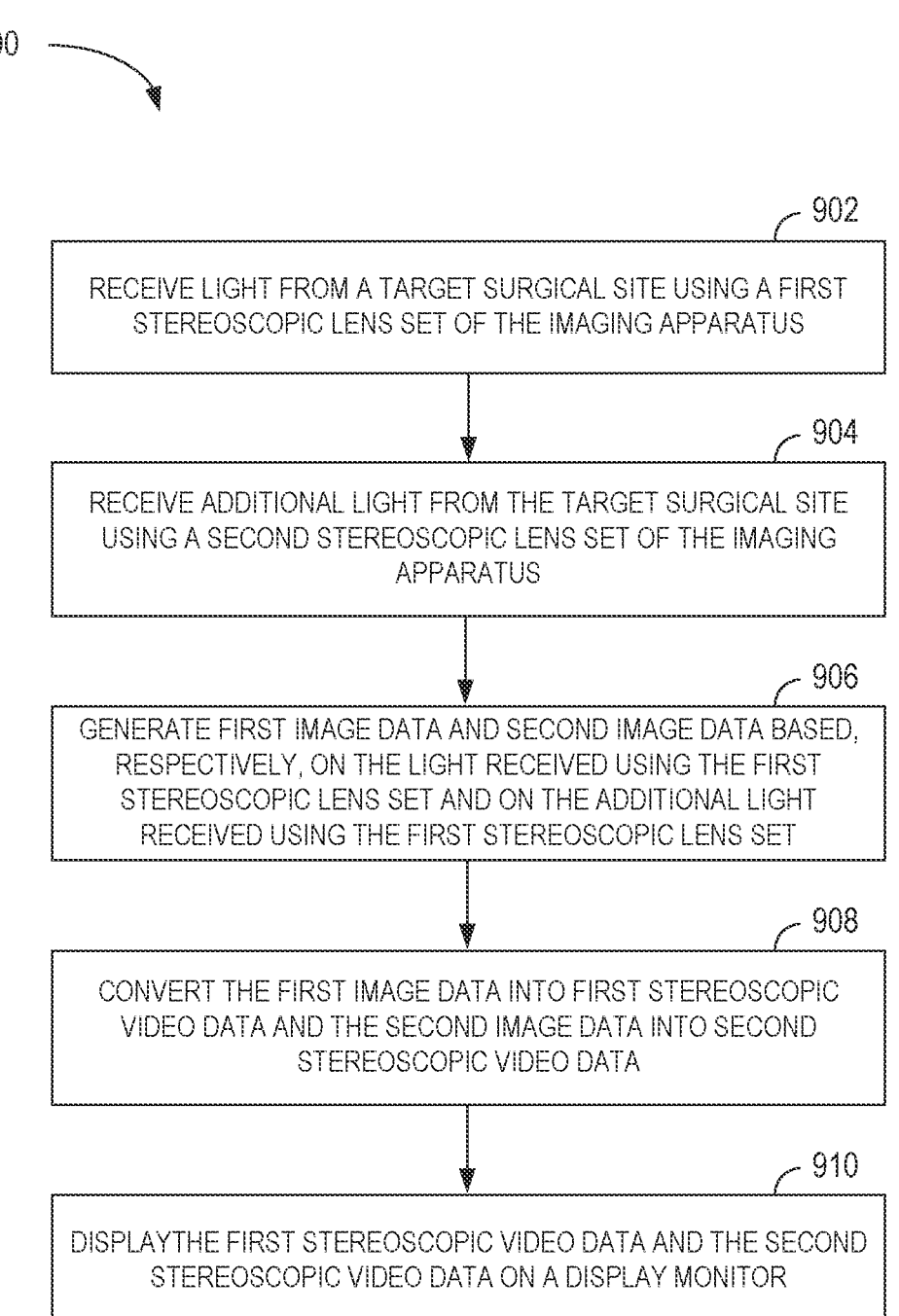

902

RECEIVE LIGHT FROM A TARGET SURGICAL SITE USING A FIRST STEREOSCOPIC LENS SET OF THE IMAGING APPARATUS

904

RECEIVE ADDITIONAL LIGHT FROM THE TARGET SURGICAL SITE USING A SECOND STEREOSCOPIC LENS SET OF THE IMAGING APPARATUS

906

GENERATE FIRST IMAGE DATA AND SECOND IMAGE DATA BASED, RESPECTIVELY, ON THE LIGHT RECEIVED USING THE FIRST STEREOSCOPIC LENS SET AND ON THE ADDITIONAL LIGHT RECEIVED USING THE FIRST STEREOSCOPIC LENS SET

908

CONVERT THE FIRST IMAGE DATA INTO FIRST STEREOSCOPIC VIDEO DATA AND THE SECOND IMAGE DATA INTO SECOND STEREOSCOPIC VIDEO DATA

910

DISPLAYTHE FIRST STEREOSCOPIC VIDEO DATA AND THE SECOND STEREOSCOPIC VIDEO DATA ON A DISPLAY MONITOR

FIG. 9

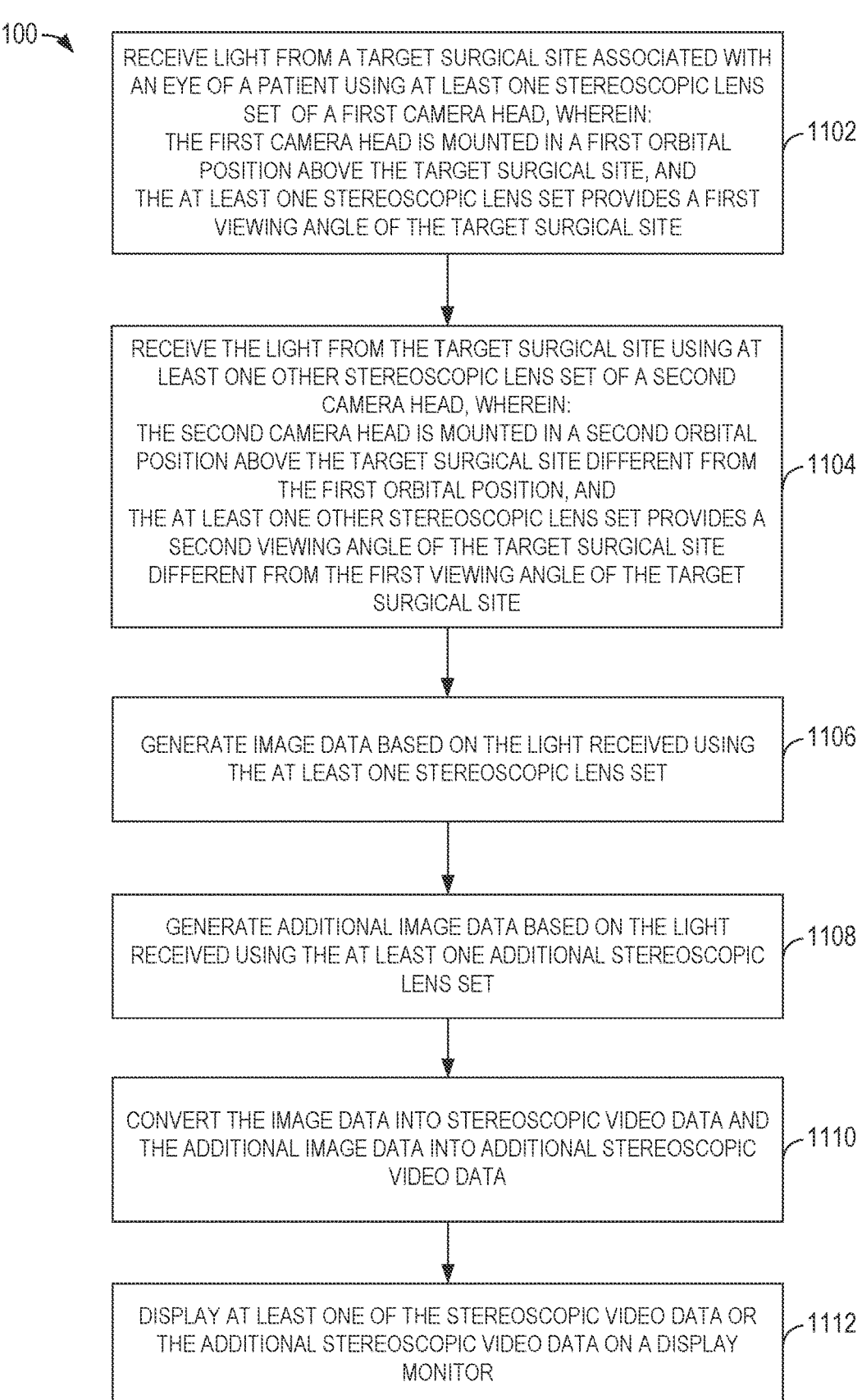

1100

RECEIVE LIGHT FROM A TARGET SURGICAL SITE ASSOCIATED WITH AN EYE OF A PATIENT USING AT LEAST ONE STEREOSCOPIC LENS SET OF A FIRST CAMERA HEAD, WHEREIN:
THE FIRST CAMERA HEAD IS MOUNTED IN A FIRST ORBITAL POSITION ABOVE THE TARGET SURGICAL SITE, AND
THE AT LEAST ONE STEREOSCOPIC LENS SET PROVIDES A FIRST VIEWING ANGLE OF THE TARGET SURGICAL SITE
— 1102

RECEIVE THE LIGHT FROM THE TARGET SURGICAL SITE USING AT LEAST ONE OTHER STEREOSCOPIC LENS SET OF A SECOND CAMERA HEAD, WHEREIN:
THE SECOND CAMERA HEAD IS MOUNTED IN A SECOND ORBITAL POSITION ABOVE THE TARGET SURGICAL SITE DIFFERENT FROM THE FIRST ORBITAL POSITION, AND
THE AT LEAST ONE OTHER STEREOSCOPIC LENS SET PROVIDES A SECOND VIEWING ANGLE OF THE TARGET SURGICAL SITE DIFFERENT FROM THE FIRST VIEWING ANGLE OF THE TARGET SURGICAL SITE
— 1104

GENERATE IMAGE DATA BASED ON THE LIGHT RECEIVED USING THE AT LEAST ONE STEREOSCOPIC LENS SET
— 1106

GENERATE ADDITIONAL IMAGE DATA BASED ON THE LIGHT RECEIVED USING THE AT LEAST ONE ADDITIONAL STEREOSCOPIC LENS SET
— 1108

CONVERT THE IMAGE DATA INTO STEREOSCOPIC VIDEO DATA AND THE ADDITIONAL IMAGE DATA INTO ADDITIONAL STEREOSCOPIC VIDEO DATA
— 1110

DISPLAY AT LEAST ONE OF THE STEREOSCOPIC VIDEO DATA OR THE ADDITIONAL STEREOSCOPIC VIDEO DATA ON A DISPLAY MONITOR
— 1112

FIG. 11

IMAGING APPARATUS WITH MULTIPLE STEREOSCOPIC CAMERAS

BACKGROUND

Surgery is art. Accomplished artists create works of art that far exceed the capabilities of a normal person. Artists use a brush to turn canisters of paint into vivid images that provoke strong and unique emotions from viewers. Artists take ordinary words written on paper and turn them into dramatic and awe-inspiring performances. Artists grasp instruments causing them to emit beautiful music. Similarly, surgeons take seemingly ordinary scalpels, tweezers, and probes and produce life-altering biological miracles.

Like artists, surgeons have their own methods and preferences. Aspiring artists are taught the fundamentals of their craft. Beginners often follow prescribed methods. As they gain experience, confidence, and knowledge, they develop their own unique artistry reflective of themselves and their personal environment. Similarly, medical students are taught the fundamentals of surgical procedures. They are rigorously tested on these methods. As the students progress through residency and professional practice, they develop derivations of the fundamentals (still within medical standards) based on how they believe the surgery should best be completed. For instance, consider the same medical procedure performed by different renowned surgeons. The order of events, pacing, placement of staff, placement of tools, and use of imaging equipment varies between each of the surgeons based on their preferences. Even incision sizes and shapes can be unique to the surgeon.

The artistic-like uniqueness and accomplishment of surgeons make them wary of surgical tools that change or alter their methods. The tool should be an extension of the surgeon, operating simultaneously and/or in harmonious synchronization. Surgical tools that dictate the flow of a procedure or change the rhythm of a surgeon are often discarded or modified to conform.

In an example, consider microsurgery visualization where certain surgical procedures involve patient structures that are too small for a human to visualize easily with the naked eye. For these microsurgery procedures, magnification is required to adequately view the microstructures. Surgeons generally want visualization tools that are natural extensions of their eyes. Indeed, early efforts at microsurgery visualization comprised attaching magnifying lens to head-mounted optical eyepieces (called surgical loupes). The first pair was developed in 1876. Vastly improved versions of surgical loupes (some including optical zooms and integrated light sources) are still being used by surgeons today. FIG. 1 shows a diagram of a pair of surgical loupes 100 with a light source 102 and magnification lenses 104a-b. The 150-year staying power of surgical loupes can be attributed to the fact that they are literally an extension of a surgeon's eyes.

Despite their longevity, surgical loupes are not perfect. Loupes with magnifying lenses and light sources, such as the surgical loupes 100 of FIG. 1, have much greater weight. Placing even a minor amount of weight on the front of a surgeon's face can increase discomfort and fatigue, especially during prolonged surgeries. The surgical loupes 100 also include a cable 106 that is connected to a remote power supply. The cable effectively acts as a chain, thereby limiting the mobility of the surgeon during their surgical performance.

Another microsurgery visualization tool is the surgical microscope, also referred to as the operating microscope.

Widespread commercial development of surgical microscopes began in the 1950s with the intention of replacing surgical loupes. Surgical microscopes include optical paths, lenses, and focusing elements that provide greater magnification compared to surgical loupes. The large array of optical elements (and resulting weight) meant that surgical microscopes had to be detached from the surgeon. While this detachment gave the surgeon more room to maneuver, the bulkiness of the surgical microscope caused it to consume considerable operating space above a patient, thereby reducing the size of the surgical stage.

FIG. 2 shows a diagram of a prior art surgical microscope 200. As one can imagine, the size and presence of the surgical microscope in the operating area made it prone to bumping. To provide stability and rigidity at the scope head 201, the microscope is connected to relatively large boom arms 202 and 204 or other similar support structure. The large boom arms 202 and 204 consume additional surgical space and reduce the maneuverability of the surgeon and staff. In total, the surgical microscope 200 shown in FIG. 2 could weigh as much as 350 kilograms ("kg").

To view a target surgical site using the surgical microscope 200, a surgeon looks directly though oculars 206. To reduce stress on a surgeon's back, the oculars 206 are generally positioned along a surgeon's natural line of sight using the boom arm 202 to adjust height. However, surgeons do not perform by only looking at a target surgical site. The oculars 206 have to be positioned such that the surgeon is within arm's length of a working distance to the patient. Such precise positioning is critical to ensure the surgical microscope 200 becomes an extension rather than a hindrance to the surgeon, especially when being used for extended periods.

Like any complex instrument, it takes surgeons tens to hundreds of hours to feel comfortable using a surgical microscope. As shown in FIG. 2, the design of the surgical microscope 200 requires a substantially 90° angle optical path from the surgeon to the target surgical site. For instance, a perfectly vertical optical path is required from the target surgical site to the scope head 201. This means that the scope head 201 has to be positioned directly above the patient for every microsurgical procedure. In addition, the surgeon has to look almost horizontally (or some slight angle downward) into the oculars 206. A surgeon's natural inclination is to direct his vison to his hands at the surgical site. Some surgeons even want to move their heads closer to the surgical site to have more precise control of their hand movements. Unfortunately, the surgical microscope 200 does not give surgeons this flexibility. Instead, surgical microscope 200 ruthlessly dictates that the surgeon is to place their eyes on the oculars 206 and hold their head at arm's length during their surgical performance, all while consuming valuable surgical space above the patient. A surgeon cannot even simply look down at a patient because the scope head 201 blocks the surgeon's view.

To make matters worse, some surgical microscopes, such as shown in surgical microscope 200, include a second pair of oculars 208 for co-performers (e.g., assistant surgeons, nurses, or other clinical staff). The second pair of oculars 208 is usually positioned at a right angle from the oculars 206. The closeness between the oculars 206 and 208 dictates that the assistant must stand (or sit) in close proximity to the surgeon, further restricting movement. This can be annoying to some surgeons who like to perform with some space. Despite their magnification benefits surgical microscopes like surgical microscope 200 are not natural extensions of a surgeon. Instead, they are overbearing directors in the surgical room. Accordingly, there is a need in the art for improved surgical microscopes.

SUMMARY

Aspects of the present disclosure provide an ophthalmic imaging apparatus. The ophthalmic imaging apparatus includes a first camera head mounted in a first orbital position above a target surgical site associated with an eye of a patient, wherein the first camera head includes at least one stereoscopic lens set providing a first viewing angle of the target surgical site. Additionally, the ophthalmic imaging apparatus includes at least a second camera head mounted in a second orbital position above the target surgical site, wherein the second camera head includes at least one additional stereoscopic lens set providing a second viewing angle of the target surgical site different from the first viewing angle of the target surgical site.

Aspects of the present disclosure provide a process for displaying stereoscopic video data of a target surgical site using an ophthalmic imaging apparatus. The process includes receiving light from a target surgical site associated with an eye of a patient using at least one stereoscopic lens set of a first camera head, wherein: the first camera head is mounted in a first orbital position above the target surgical site, and the at least one stereoscopic lens set provides a first viewing angle of the target surgical site. The process further includes receiving the light from the target surgical site using at least one other stereoscopic lens set of a second camera head, wherein: the second camera head is mounted in a second orbital position above the target surgical site different from the first orbital position, and the at least one other stereoscopic lens set provides a second viewing angle of the target surgical site different from the first viewing angle of the target surgical site. The process further includes generating image data based on the light received using the at least one stereoscopic lens set, generating additional image data based on the light received using the at least one other stereoscopic lens set, converting the image data into stereoscopic video data and the additional image data into additional stereoscopic video data, and displaying at least one of the stereoscopic video data or the additional stereoscopic video data on a display monitor.

The above-described features and advantages and other possible features and advantages of the present disclosure will be apparent from the following detailed description of the best modes for carrying out the disclosure when taken in connection with the accompanying drawings.

BRIEF DESCRIPTION OF THE DRAWINGS

The drawings described herein are for illustrative purposes only, are schematic in nature, and are intended to be exemplary rather than to limit the scope of the disclosure.

FIG. 9 shows an example process for simultaneously displaying different stereoscopic video data of a target surgical site.

FIG. 11 shows an example process for displaying different stereoscopic video data associated with different viewing angles of a target surgical site.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

Figure 1:
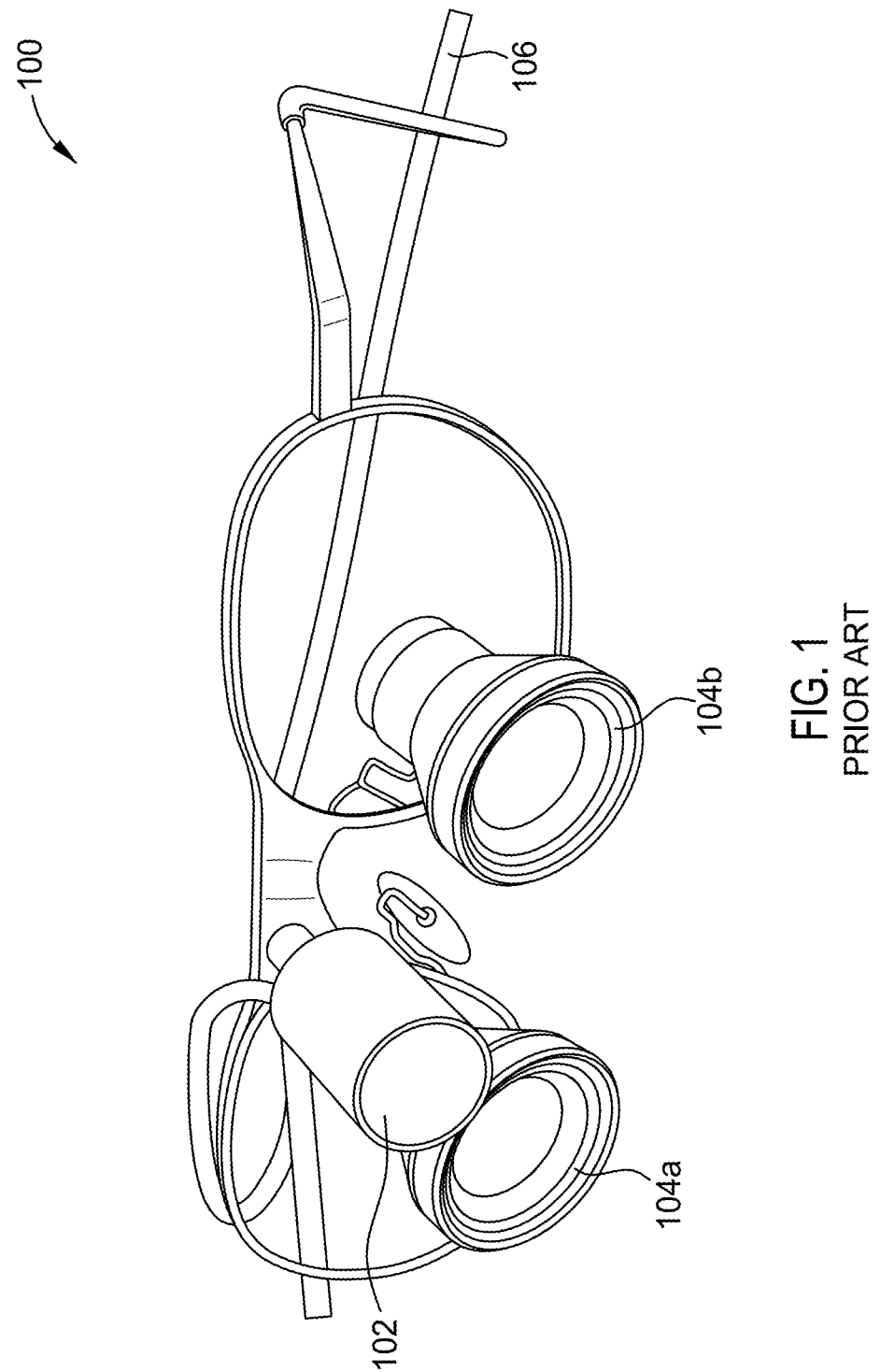
FIG. 1 shows a diagram of a pair of prior art surgical loupes.
Figure 2:
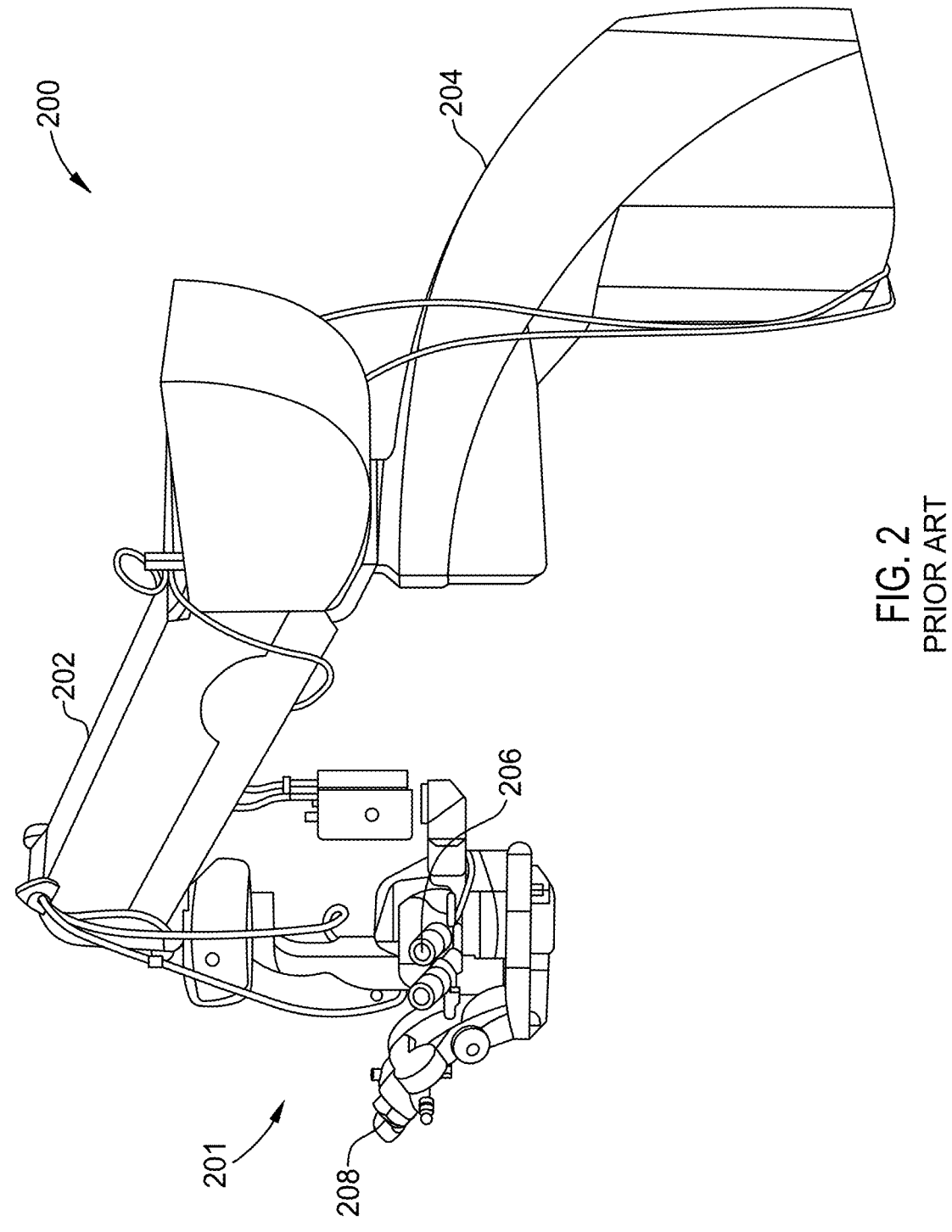
FIG. 2 shows a diagram of a prior art surgical microscope.

The present disclosure relates in general to an imaging apparatus and platform. The imaging apparatus may be referred to, in some cases, as a digital stereoscopic microscope ("DSM"). The example imaging apparatus and platform are configured to integrate microscope optical elements and video sensors into a self-contained head unit or housing that is significantly smaller, lighter, and more maneuverable than prior art microscopes (such as the surgical loupes 100 of FIG. 1 and the surgical microscope 200 of FIG. 2). The example camera is configured to transmit/display stereoscopic video data to/on one or more television monitors, display monitors, projectors, holographic devices, smart-glasses, virtual reality devices, or other visual display devices within a surgical environment.

The monitors or other visual display devices may be positioned within the surgical environment to be easily within a surgeon's line of sight while performing surgery on a patient. This flexibility enables the surgeon to place display monitors based on personal preferences or habits. In addition, the flexibility and slim profile of the stereoscopic visualization camera disclosed herein reduces area consumed over a patient. Altogether, the stereoscopic visualization camera and monitors (e.g., the stereoscopic visualization platform) enable a surgeon and surgical team to perform complex microsurgical procedures on a patient without being dictated or restricted in movement compared to the surgical microscope 200 discussed above. The example stereoscopic visualization platform accordingly operates as an extension of the surgeon's eyes, enabling the surgeon to perform masterpiece microsurgeries without dealing with the stress, restrictions, and limitations induced by previous known visualization systems.

Aspects of the present disclosure provide techniques for enabling the display of different stereoscopic video data associated with different fields-of-view and magnification levels of a target surgical site. For example, certain surgical microscopes, such as the stereoscopic visualization camera 300 illustrated in FIG. 3 and described below, achieve these different fields-of-view and magnification levels of the target surgical site using multiple fixed focal length lenses that move forward and backward along rails.

In certain cases, moving zoom lenses are heavy, expensive, and include sensitive optics prone to focusing issues, which makes the stereoscopic visualization camera more difficult and more expensive to manufacture. Additionally, the parts that move the zoom lenses (e.g., motors, rails, etc.) are prone to wearing down and breaking, which can lead to costly repairs. Moreover, a surgeon may only be able to view one field-of-view/magnification level of the target surgical site at a time and may have to pause surgery to switch fields-of-view/magnification levels (e.g., to wait for the zoom lenses to move), causing delays in the surgery and slowing down workflow.

Accordingly, aspects of the present disclosure provide an ophthalmic imaging apparatus that includes a plurality of stereoscopic lens sets each associated with a different fixed magnification level. Each of these different fixed magnification levels may be associated with a different field-of-view of a target surgical site, which may be simultaneously displayed to a surgeon on a display monitor. By providing multiple lens sets associated with different magnification levels and simultaneously displaying corresponding fields-of-view, the surgeon does not need to pause surgery to change the magnification level/field-of-view. Moreover, because the magnification levels are fixed, the stereoscopic imaging device may not require moving parts, avoiding complex and expensive manufacture and repair.

Aspects of the present disclosure provide techniques for enabling the display of different stereoscopic video data associated with viewing angles of a target surgical site. These different viewing angles are especially important in certain types of surgeries, such as retinal and cataract surgeries. Using traditional techniques to achieve these different viewing angles involved techniques, such as moving a patients head and scleral depression. Newer techniques involve the use of a surgical microscope with a camera head that is able to move to different orbital positions above the target surgical site. However, these techniques slow down a surgeon's workflow, leading to longer surgeries. Additionally, in some cases, certain techniques, such as scleral depression can lead to additional trauma caused to the patient. Additionally, surgical microscopes with moving camera heads are costly to manufacture and prone to malfunction, leading to costly repairs and long down-times.

Accordingly, aspects of the present disclosure provide an ophthalmic imaging apparatus that includes a plurality of camera heads mounted in different orbital positions above a target surgical site. Each camera head of the plurality of camera heads may be configured to provide a different viewing angle of the target surgical site. By providing multiple camera heads associated with different viewing angles of the target surgical site and displaying different fields-of-view of the target surgical site corresponding to these different viewing angles, the surgeon does not need to pause surgery to move a patient's head to obtain a peripheral view of the target surgical site or correct alignment issues when moving the patient's head back. Nor does the surgeon need to perform scleral depression, eliminating the potential additional trauma to the patient associated with scleral depression. Further, providing multiple camera heads mounted in different orbital positions above the target surgical site eliminates the need for the parts that facilitate the physical movement of the single camera of these certain surgical microscopes, avoiding the manufacturing expense as well as the complex and costly repairs of such moving parts.

The disclosure herein generally refers to microsurgery. The example stereoscopic visualization camera may be used in virtually any microsurgical procedure including, for example, cranial surgery, brain surgery, neurosurgery, spinal surgery, ophthalmologic surgery, corneal transplants, orthopedic surgery, ear, nose and throat surgery, dental surgery, plastics and reconstructive surgery, or general surgery.

The disclosure also refers herein to target surgical site, scene, or field-of-view. As used herein, target surgical site or field-of-view includes an object (or portion of an object) that is being recorded or otherwise imaged by the example stereoscopic visualization camera. Generally, the target surgical site, scene, or field-of-view is a working distance away from a main objective assembly of the example stereoscopic visualization camera and is aligned with the example stereoscopic visualization camera. The target surgical site may include a patient's biological tissue, bone, muscle, skin or combinations thereof. In these instances, the target surgical site may be three-dimensional by having a depth component corresponding to a progression of a patient's anatomy. The target surgical site may also include one or more templates used for calibration or verification of the example stereoscopic visualization camera. The templates may be two-dimensional, such as a graphic design on paper (or plastic sheet) or three dimensional, such as to approximate a patient's anatomy in a certain region.

Reference is also made throughout to an x-direction, a y-direction, a z-direction, and a tilt-direction. The z-direction is along an axis from the example stereoscopic visualization camera to the target surgical site and generally refers to depth. The x-direction and y-direction are in a plane incident to the z-direction and comprise a plane of the target surgical site. The x-direction is along an axis that is 90° from an axis of the y-direction. Movement along the x-direction and/or the y-direction refers to in-plane movement and may refer to movement of the example stereoscopic visualization camera, movement of optical elements within the example stereoscopic visualization camera, and/or movement of the target surgical site.

Example Stereoscopic Visualization Camera

Figure 3:
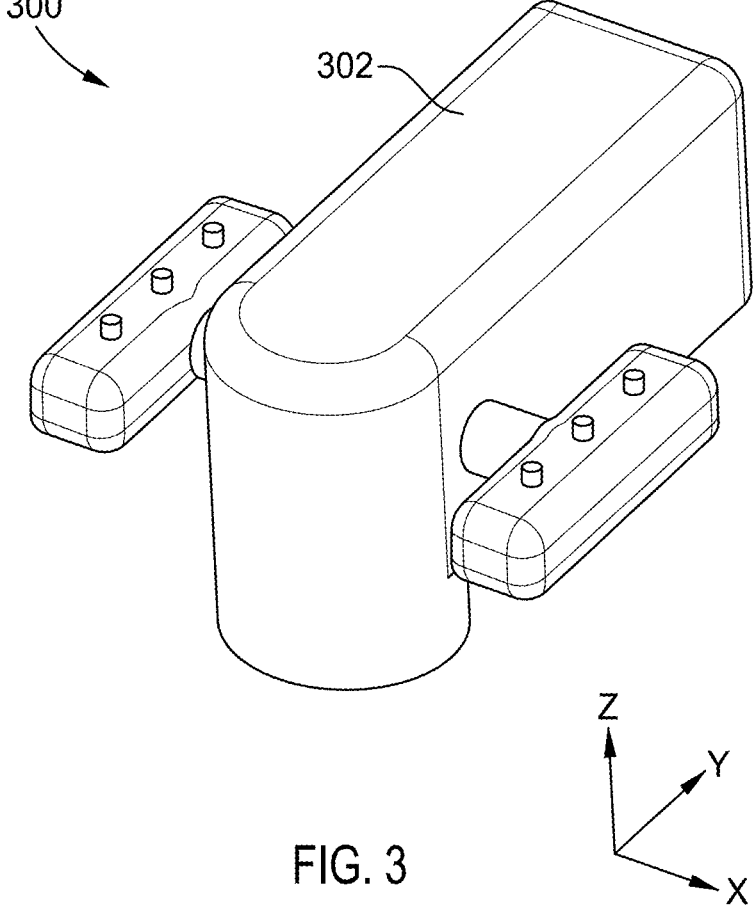
FIG. 3 shows a perspective view of a stereoscopic visualization camera.
Figure 4:
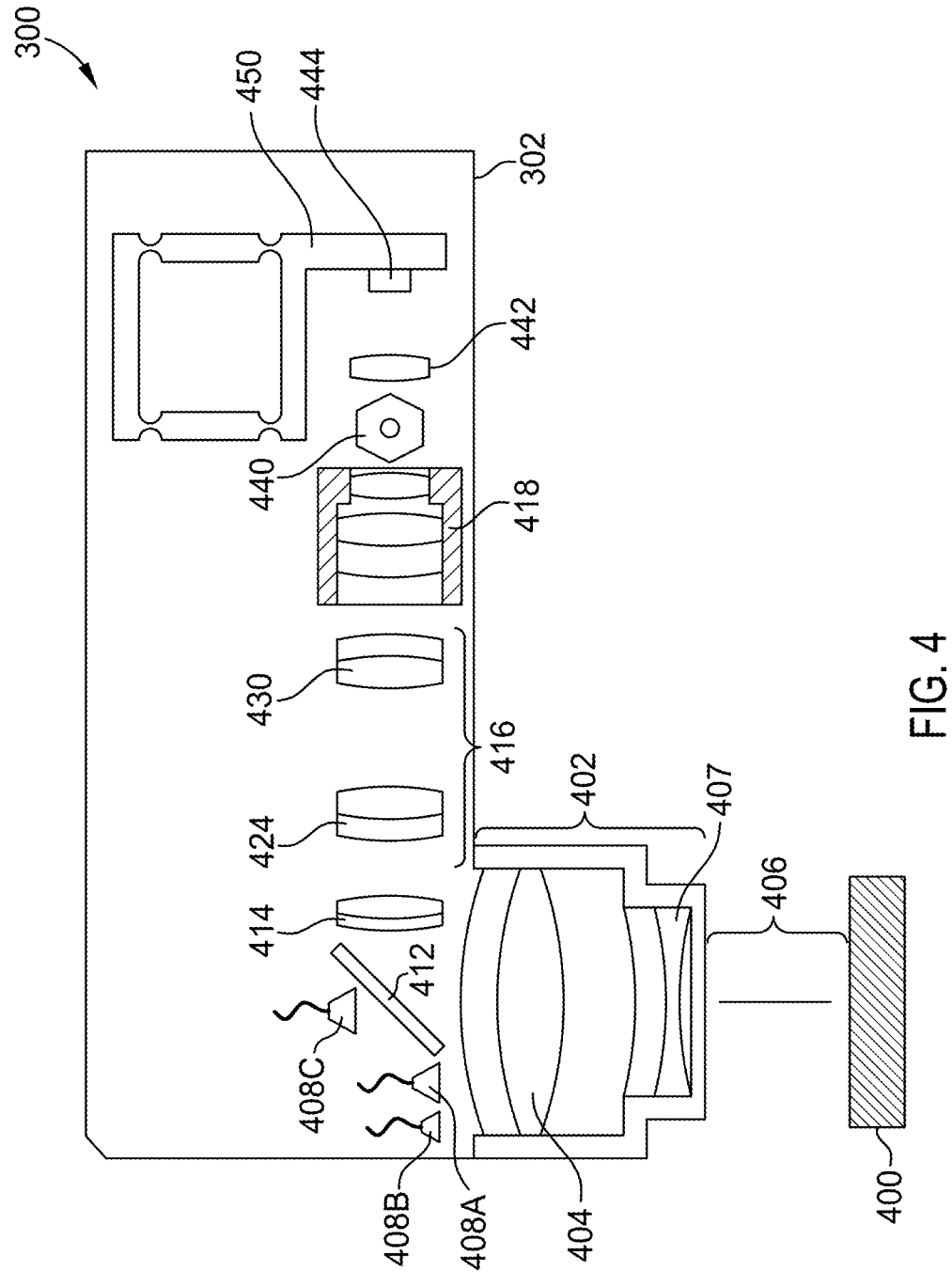
FIG. 4 shows a diagram illustrative of optical elements within the example stereoscopic visualization camera.

FIG. 3 illustrates a perspective view of a stereoscopic visualization camera 300. As shown in FIG. 3, the stereoscopic visualization camera 300 includes a housing 302 configured to enclose optical elements, lens motors (e.g., actuators), and signal processing circuity. FIG. 4 shows an example arrangement and positioning of the optical elements of the stereoscopic visualization camera 300. In some cases, the arrangement and positioning of the optical elements of the stereoscopic visualization camera 300 forms two parallel optical paths to generate a left view and a right view. The parallel optical paths correspond to a human's visual system such that the left view and right view, as displayed on a stereoscopic display, appear to be separated by a distance that creates a convergence angle of, for example, roughly 6 degrees, which is comparable to the convergence angle for an adult human's eyes viewing an object at approximately 4 feet away, thereby resulting in stereopsis. In some embodiments, image data generated from the left view and right view are combined together on the display monitor(s) to generate a stereoscopic image of a target surgical site or scene.

A stereoscopic view, as compared to a monoscopic view, mimics the human visual system much more closely. A stereoscopic view provides depth perception, distance perception, and relative size perception to provide a realistic view of a target surgical site to a surgeon. For procedures such as retinal surgery, stereoscopic views are useful because surgical movements and forces are so small that the surgeon cannot feel them. Providing a stereoscopic view helps a surgeon's brain magnify tactile feel when the brain senses even minor movements while perceiving depth.

FIG. 4 shows a side view of the example stereoscopic visualization camera 300 with the housing 302 being transparent to expose the optical elements. The optical elements shown in FIG. 4 may be part of a left optical path and may generate the left view. It should be appreciated that the arrangement and positioning of optical elements in a right optical path in stereoscopic visualization camera 300 (e.g., generating the right view) may generally be identical to the left optical path.

The example stereoscopic visualization camera 300 is configured to acquire images of a target surgical site 400 (also referred to as a scene or field-of-view) at a working distance 406 above the target surgical site 400. The target surgical site 400 includes an anatomical location on a patient. The target surgical site 400 may also include laboratory biological samples, calibration slides/templates, etc. Images from the target surgical site 400 are received at the stereoscopic visualization camera 300 via a main objective assembly 402, which includes the front working distance lens 407 and a rear working distance lens 404.

To illuminate the target surgical site 400, the example stereoscopic visualization camera 300 includes one or more lighting sources, such as a near-infrared ("NIR") light source 408b, and a near-ultraviolet ("NUV") light source 408c. In other examples, the stereoscopic visualization camera 300 may include additional or fewer (or no) light sources. For instance, the NIR and NUV light sources may be omitted. The example light sources 408 are configured to generate light, which is projected to the target surgical site 400. The generated light interacts and reflects off the target scene, with some of the light being reflected to the main objective assembly 402. Other examples may include external light sources or ambient light from the environment.

The projection of the light from light sources 408 through the main objective assembly provides the benefit of changing the lighted field-of-view based on the working distance 406 and/or focal plane. Since the light passes through the main objective assembly 402, the angle at which light is projected changes based on the working distance 406 and corresponds to the angular field-of-view. This configuration accordingly ensures the field-of-view is properly illuminated by the light sources 408, regardless of working distance or magnification.

Further, as illustrated in FIG. 4, the stereoscopic visualization camera 300 includes a deflecting element 412. In some cases, the deflecting element 412 may be configured to transmit a certain wavelength of light from the NUV light source 408c to the target surgical site 400 through the main objective assembly 402. The deflecting element 412 may also be configured to reflect light received from the target surgical site 400 to downstream optical elements, including a front lens set 414 for zooming and recording. In some embodiments, the deflecting element 412 may filter light received from the target surgical site 400 through the main objective assembly 402 so that light of certain wavelengths reaches the front lens set 414.

The deflecting element 412 may include any type of mirror or lens to reflect light in a specified direction. In an example, the deflecting element 412 includes a dichroic mirror or filter, which has different reflection and transmission characteristics at different wavelengths. The stereoscopic visualization camera 300 of FIG. 4 includes a single deflecting element 412, which provides light for both the right and left optical paths. In other examples, the stereoscopic visualization camera 300 may include separate deflecting elements for each of the right and left optical paths. Further, a separate deflecting element may be provided for the NUV light source 408c.

The example stereoscopic visualization camera 300 of FIG. 4 includes one or more zoom lens to change a focal length and angle of view of the target surgical site 400 to provide zoom magnification. In the illustrated example of FIG. 4, the zoom lens includes the front lens set 414, a zoom lens assembly 416, and a lens barrel set 418. In some cases, the zoom lens may include additional lens(es) to provide further magnification and/or image resolution.

The front lens set 414 includes a right front lens for the right optical path and a left front lens for the left optical path. The lenses left and right front lenses may each include a positive converging lens to direct light from the deflecting element 412 to respective lenses in the zoom lens assembly 416. A lateral position of the left and right front lenses accordingly defines a beam from the main objective assembly 402 and the deflecting element 412 that is propagated to the zoom lens assembly 416.

The example zoom lens assembly 416 forms an afocal zoom system for changing the size of a field-of-view (e.g., a linear field-of-view) by changing a size of the light beam propagated to the lens barrel set 418. The zoom lens assembly 416 includes a front zoom lens set 424 with a right front zoom lens and a left front zoom lens. The zoom lens assembly 416 also includes a rear zoom lens set 430 with a right rear zoom lens and a left rear zoom lens.

The size of an image beam for each of the left and right optical paths is determined based on a distance between the front zoom lenses in the front zoom lens set 424, the rear zoom lenses in the rear zoom lens set 430, and the lens barrel set 418. Generally, the size of the optical paths reduces as the rear zoom lenses in the rear zoom lens set 430 move toward the lens barrel set 418 (along the respective optical paths), thereby decreasing magnification. In addition, the front zoom lenses in the front zoom lens set 424 may also move toward (or away from) the lens barrel set 418 (such as in a parabolic arc), as the rear zoom lenses in the rear zoom lens set 430 move toward the lens barrel set 418, to maintain the location of the focal plane on the target surgical site 400, thereby maintaining focus.

The front zoom lenses in the front zoom lens set 424 may be included within a first carrier while the rear zoom lenses in the rear zoom lens set 430 are included within a second carrier. Each of the carriers may be moved on tracks (or rails) along the optical paths such left and right magnification may be uniformly adjusted (e.g., increased or decreased). Altogether, the front lens set 414, the zoom lens assembly 416, and the lens barrel set 418 are configured to achieve an optical zoom, such as between 5× to about 20×, such as at a zoom level that has diffraction-limited resolution.

After the light from the target surgical site 400, the light in each of the right and left optical paths may pass through one or more optical filters 440 (or filter assemblies) to selectively transmit desired wavelengths of light. The light in each of the right and left optical paths may then pass through a final optical element set 442 that is configured to focus light received from the optical filter 440 onto the optical image sensor 444.

As shown, the stereoscopic visualization camera 300 of FIG. 4 includes the optical image sensor 444, which may be configured to acquire and/or record incident light that is received from the final optical element set 442. The optical image sensor 444 includes a right optical image sensor configured to record light propagating along the right optical path and generate right image data associated with the right optical path. Additionally, the optical image sensor 444 also includes a left optical image sensor configured to record light propagating along the left optical path and generate left image data associated with the left optical path. After the right and left image data are created, one or more processors may synchronize and combine the left and right image data to generate a stereoscopic image. Additionally, the one or more processors may be configured to convert a plurality of stereoscopic images into stereoscopic video data for display to a user of the stereoscopic visualization camera 300 on a display monitor, such as a stereoscopic display.

Additional aspects of the stereoscopic visualization camera 300 may be found in U.S. Pat. No. 11,058,513, titled "STEREOSCOPIC VISUALIZATION CAMERA AND PLATFORM," the entirety of which is incorporated herein by reference.

Figure 5:
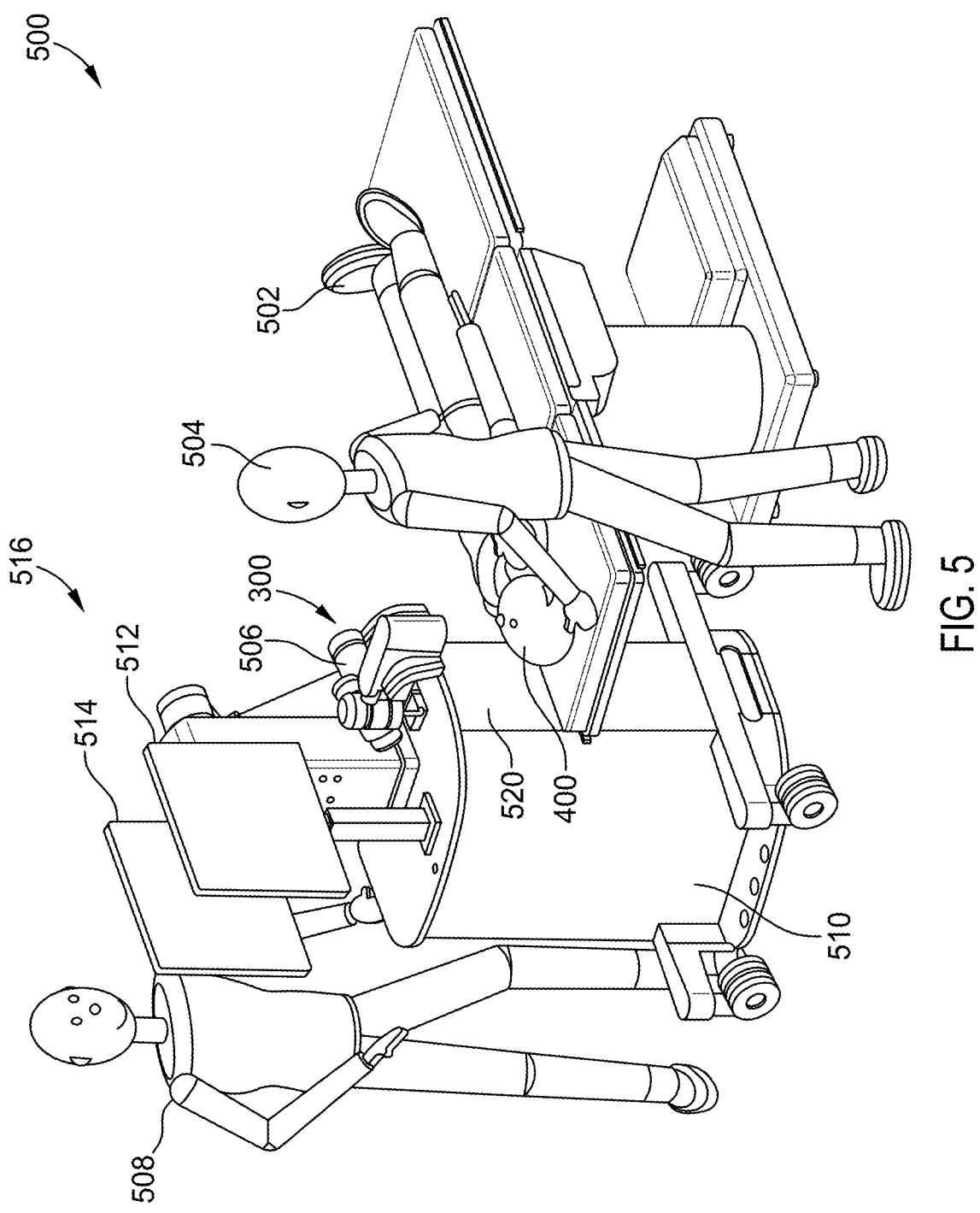
FIG. 5 shows a diagram of a microsurgical environment including the stereoscopic visualization camera.

FIG. 5 shows a diagram of the stereoscopic visualization camera 300 used within a microsurgical environment 500. In some embodiments, the microsurgical environment 500 of FIG. 5 may be used for an ophthalmic surgery procedure. As illustrated, the small footprint and maneuverability of the stereoscopic visualization camera 300 (especially when used in conjunction with a multiple-degree of freedom arm) enables flexible positioning with respect to a patient 502. A portion of the patient 502 in view of the stereoscopic visualization camera 300 includes the target surgical site 400. A surgeon 504 can position the stereoscopic visualization camera 300 in virtually any orientation while leaving more than sufficient surgical space above the patient 502 (lying in the supine position). The stereoscopic visualization camera 300 accordingly is minimally intrusive (or not intrusive) to enable the surgeon 504 to perform a life-altering microsurgical procedure without distraction or hindrance.

In FIG. 5, the stereoscopic visualization camera 300 is connected to a mechanical arm 506 (e.g., also referred to a "robot arm"). The mechanical arm 506 may include one or more rotational or extendable joints with electromechanical brakes to facilitate easy repositioning of the stereoscopic visualization camera 300. To move the stereoscopic visualization camera 300, the surgeon 504, or the assistant 508, actuates brake releases on one or more joints of the mechanical arm 506. After the stereoscopic visualization camera 300 is moved into a desired position, the brakes may be engaged to lock the joints of the mechanical arm 506 in place.

A significant feature of the stereoscopic visualization camera 300 is that it does not include oculars. This means that the stereoscopic visualization camera 300 does not have to be aligned with the eyes of the surgeon 504. This freedom enables the stereoscopic visualization camera 300 to be positioned and orientated in desirable positions that were not practical or possible with prior known surgical microscopes. In other words, the surgeon 504 can perform microsurgery with, for example, the most optimal view for conducting the procedure rather than being restricted to a merely adequate view dictated by oculars of a surgical microscope.

As shown in FIG. 5, the stereoscopic visualization camera 300, via the mechanical arm 506, is connected to a cart 510 with display monitors 512 and 514 (collectively a stereoscopic visualization platform 516). In the illustrated configuration, the stereoscopic visualization platform 516 is self-contained and may be moved to any desired location in the microsurgical environment 500 including between surgical rooms. The integrated stereoscopic visualization platform 516 enables the stereoscopic visualization camera 300 to be moved and used on-demand without time needed to configure the system by connecting the display monitors 512 and 514.

Each of the display monitors 512 and 514 may include any type of display including a high-definition television, an ultra-high definition television, smart-eyewear, a projector, one or more computer screens, a laptop computer, a tablet computer, and/or a smartphone. The display monitors 512 and 514 may be connected to mechanical arms to enable flexible positioning similar to the stereoscopic visualization camera 300. In some instances, one or more of the display monitors 512 and 514 may include a touchscreen to enable an operator to send commands to the stereoscopic visualization camera 300 and/or adjust a setting of a display.

In some embodiments, the cart 510 may include a computer 520. In these embodiments, the computer 520 may control a robotic mechanical arm connected to the stereoscopic visualization camera 300. Additionally or alternatively, the computer 520 may process video (or stereoscopic video) signals (e.g., an image or frame stream) from the stereoscopic visualization camera 300 for display on the display monitors 512 and 514. For example, the computer 520 may combine or interleave left and right video signals from the stereoscopic visualization camera 300 to create a stereoscopic signal for displaying a stereoscopic image of a target surgical site. The computer 520 may also be used to store video and/or stereoscopic video signals into a video file (stored to a memory) so the surgical performance can be documented and played back. Further, the computer 520 may also send control signals to the stereoscopic visualization camera 300 to select settings and/or perform calibration.

Aspects Related to a Stereoscopic Imaging Apparatus with Multiple Fixed Magnification Levels Digital stereoscopic microscopes, such as the stereoscopic visualization camera 300, are especially useful when performing eye surgery. Typically, in surgical microscopes, such as the stereoscopic visualization camera 300, multiple zoom or magnification levels are accomplished by designing the surgical microscope to have moving zoom lens groups, such as the front and rear zoom lenses in the a zoom lens assembly 416 of the stereoscopic visualization camera 300 illustrated in FIG. 4. For example, as the front and rear zoom lenses in the zoom lens assembly 416 move forward and backward along rails, light from the target surgical site 400 passing through the these lenses focuses at different distances, resulting in different zooms or magnification levels. However, moving zoom lenses are heavy, expensive, and include sensitive objects prone to focusing issues, which makes the stereoscopic visualization camera 300 more difficult and more expensive to manufacture. Additionally, the parts that move the zoom lenses (e.g., motors, rails, etc.) are prone to wearing down and breaking, which can lead to costly repairs.

Moreover, moving zoom lenses are capable of producing only one magnification level at any given point in time. As a result, only one field-of-view of the target surgical site 400 may be displayed to a surgeon (e.g., surgeon 504 in FIG. 5) at any given point. This may be problematic since, during surgery, surgeons change between different zoom/magnification levels in order to accomplish various tasks. For example, larger zooms/greater magnification (e.g., resulting in a narrow field-of-view of the target surgical site 400) may be used when minute details of the target surgical site need to be seen while performing difficult surgical movements. In contrast, lower zooms/less magnification may be used when a "bigger picture" view of the target surgical site 400 is needed, for example, during instrument insertion/exchange. However, in order to change zoom/magnification level, the surgeon must pause during surgery and wait for the moving lenses to adjust to a proper zoom/magnification level, causing delays in the surgery and slowing down workflow.

Accordingly, aspects of the present disclosure provide an ophthalmic imaging apparatus that includes a plurality of stereoscopic lens sets each associated with a different fixed magnification level. Each of these different fixed magnification levels may be associated with a different field-of-view of a target surgical site, which may be simultaneously displayed to a surgeon on a display monitor. For example, in some embodiments, the ophthalmic imaging apparatus may include a first stereoscopic lens set associated with a first fixed magnification level and a first field-of-view, such as a narrow field-of-view showing minute details of the target surgical site. Additionally, the ophthalmic imaging apparatus may include a second lens set associated with a second fixed magnification level and second field-of-view, such as a broad field of view showing a "bigger picture" of the target surgical site.

Accordingly, these different field-of-views of the target surgical site may be simultaneously displayed to the surgeon on a display monitor. In some embodiments, these different field-of-views may be displayed using a picture-in-picture (PIP) configuration or side by side. By providing multiple lens sets associated with different fixed magnification levels and simultaneously displaying corresponding fields-of-view, the surgeon does not need to pause surgery to change the magnification level/field-of-view. Moreover, because the magnification levels are fixed, the stereoscopic imaging device may not require moving parts, avoiding the complex and expensive manufacture and repair.

It should be understood that a stereoscopic lens set with a fixed magnification level refers to a stereoscopic lens set that is designed to a certain magnification level or focal length while including components that allow for making minor adjustments to the designed magnification level for fine focus. Accordingly, while each of the first and the second stereoscopic lens sets are designed to a different fixed magnification level, the first and the second stereoscopic lens sets may each include certain components that allow for minor adjustments to be made to the fixed magnification levels to enable fine focusing.

Figure 6A:
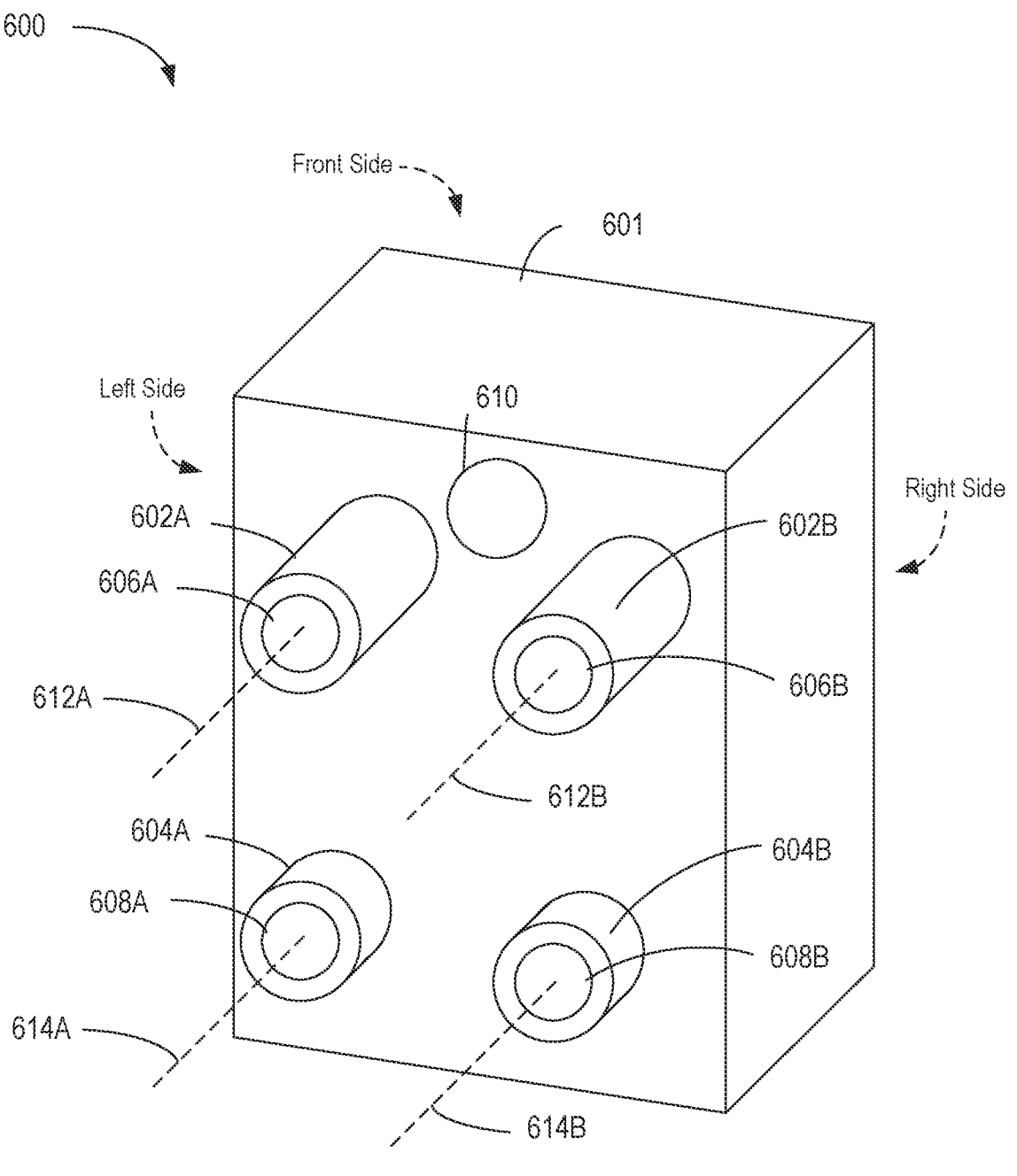
FIGS. 6A-6C show different views of an imaging apparatus that includes a plurality of stereoscopic lens sets each associated with a different fixed magnification level.
Figure 6B:
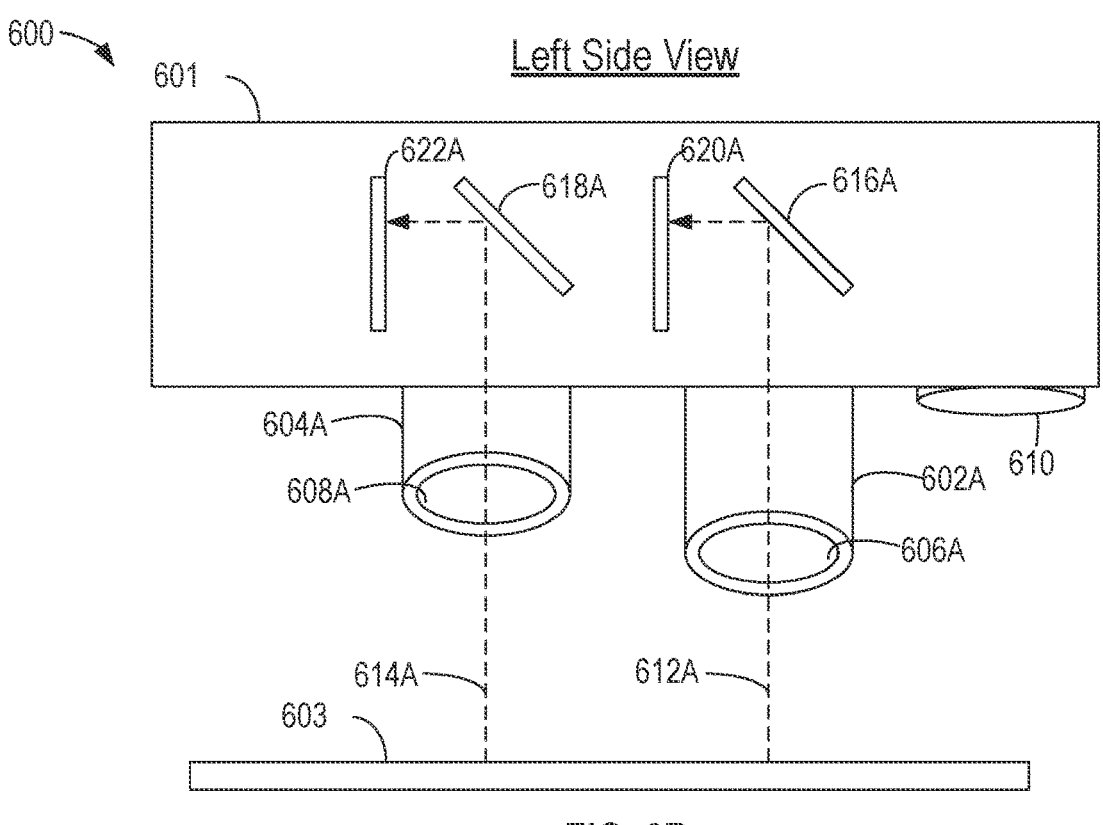
Figure 6C:
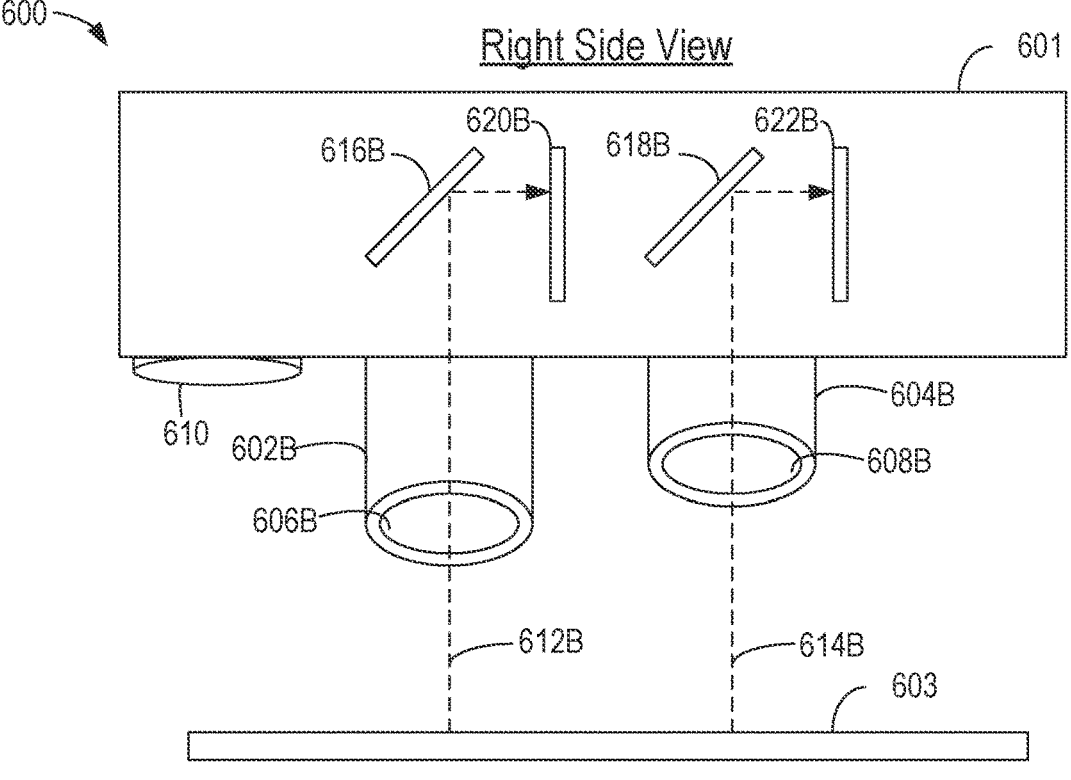

FIGS. 6A, 6B, and 6C respectively illustrate a perspective view, as left-side view, and a right-side view of an imaging apparatus 600 that includes a plurality of stereoscopic lens sets each associated with a different fixed magnification level. In some embodiments, the imaging apparatus 600 may be implemented in a microsurgical environment, such as the microsurgical environment 500. More specifically, in some embodiments, the imaging apparatus 600 is configured to replace the stereoscopic visualization camera 300 in the microsurgical environment 500.

As illustrated, the imaging apparatus 600 includes a housing 601 configured to enclose optical elements and signal processing circuity. Further, as illustrated, the imaging apparatus 600 includes a first stereoscopic lens set configured to receive light from a target surgical site 603, which may be an example of the target surgical site 400 illustrated in FIG. 4. In some embodiments, the target surgical site 603 may be associated with an eye of a patient.

In some embodiments, the received light may be generated by a light source 610. For example, the light source 610 may be configured to emit light on to the target surgical site 603. In some embodiments, the light source 610 may be an example of one or more of the light sources 408A-408C illustrated in FIG. 4.

As illustrated, the first stereoscopic lens set may include at least a first left lens barrel 602A and a first right lens barrel 602B. As shown, the first left lens barrel 602A and the first right lens barrel 602B define respective first parallel left and right optical paths, such as the first left optical path 612A and the first right optical path 612B. The first left lens barrel 602A and the first right lens barrel 602B are configured to receive light from slightly different perspectives of the target surgical site 603, providing a stereoscopic view of the target surgical site 603.

Additionally, as illustrated, the imaging apparatus 600 also includes a second stereoscopic lens set configured to receive additional light from the target surgical site generated by the light source 610. For example, the second stereoscopic lens set may include a second left lens barrel 604A and a second right lens barrel 604B. As shown, the second left lens barrel 604A and the second right lens barrel 604B define respective second parallel left and right optical paths, such as the second left optical path 614A and the second right optical path 614B. Similar to the first left lens barrel 602A and the first right lens barrel 602B, the second left lens barrel 604A and the second right lens barrel 604B are configured to receive light from the target surgical site 603 at the slightly different angles, providing another stereoscopic view of the target surgical site 603.

Further, in some embodiments, the first left lens barrel 602A and the first right lens barrel 602B of the first lens set include a first set of fixed focal length lenses configured to magnify the received light from the target surgical site 603 according to a first fixed magnification level. More specifically, as shown, the first left lens barrel 602A includes the first left fixed focal length lens 606A and the first right lens barrel 602B includes the first right fixed focal length lens 606B. Each of the fixed focal length lenses 606A and 606B are configured to magnify the received light from the target surgical site 603 according to the first fixed magnification level. In some embodiments, the first fixed magnification level may depend on a focal length associated with the fixed focal length lenses 606A and 606B and may provide a first field-of-view of the target surgical site 603. For example, in some embodiments, the first fixed magnification level of the fixed focal length lenses 606A and 606B may provide a narrow field-of-view showing minute details of the target surgical site 603. Because the fixed focal length lenses 606A and 606B are associated with a fixed magnification level, the imaging apparatus 600 may not require moving parts (e.g., motors, rails, etc.) in order to achieve the narrow field-of-view of the target surgical site. It should be understood that, while the fixed focal length lenses 606A and 606B are designed to a first fixed magnification level or focal length, the first left lens barrel 602A and the first right lens barrel 602B may each include certain components that allow for minor adjustments to be made to the first fixed magnification level to enable fine focusing.

Additionally, in some embodiments, the second left lens barrel 604A and the second right lens barrel 604B of the second lens set include a second set of fixed focal length lenses configured to magnify the received additional light from the target surgical site 603 according to a second fixed magnification level different from the first fixed magnification level. More specifically, as shown, the second left lens barrel 604A includes the second left fixed focal length lens 608A and the second right lens barrel 604B includes the second right fixed focal length lens 608B. Each of the fixed focal length lenses 608A and 608B are configured to magnify the received light from the target surgical site 603 according to the second fixed magnification level. In some embodiments, the second fixed magnification level may depend on a focal length associated with the fixed focal length lenses 608A and 608B and may provide a second field-of-view of the target surgical site 603. For example, in some embodiments, the second fixed magnification level of the fixed focal length lenses 608A and 608B may provide a "bigger picture" or wide field-of-view showing larger/wider details of the target surgical site 603. Because the fixed focal length lenses 608A and 608B are associated with a fixed magnification level, the imaging apparatus 600 may not require moving parts (e.g., motors, rails, etc.) in order to achieve the "bigger picture"/wide field-of-view of the target surgical site. It should be understood that, while the fixed focal length lenses 608A and 608B are designed to a second fixed magnification level, the second left lens barrel 604A and the second right lens barrel 604B may each include certain components that allow for minor adjustments to be made to the second fixed magnification level to enable fine focusing.

Further, the imaging apparatus 600 may include a first plurality of dichroic mirrors and a second a second plurality of dichroic mirrors. As illustrated in FIG. 6B, the first plurality of dichroic mirrors may include a first left dichroic mirror 616A associated with the first left lens barrel 602A. Additionally, as illustrated in FIG. 6C, the first plurality of dichroic mirrors may include a first right dichroic mirror 616B associated with the first right lens barrel 602B. Further, as illustrated in FIG. 6B, the second plurality of dichroic mirrors may include a second left dichroic mirror 618A associated with the second left lens barrel 604A. Additionally, as illustrated in FIG. 6C, second plurality of dichroic mirrors may include a second right dichroic mirror 618B associated with the second right lens barrel 604B.

In some embodiments, the first plurality of dichroic mirrors is configured to direct the received light from the first left lens barrel 602A and first right lens barrel 602B to a first plurality of image sensors of the imaging apparatus 600. For example, the first plurality of image sensors may include a first left image sensor 620A associated with the first left lens barrel 602A and a first right image sensor 620B associated with the first right lens barrel 602B. Accordingly, the first left dichroic mirror 616A and the first right dichroic mirror 616B may be configured to direct the received light to the first left image sensor 620A and first right image sensor 620B, respectively, along the first parallel left and right optical paths (e.g., along the first left optical path 612A and the first right optical path 612B).

Further, the second plurality of dichroic mirrors is configured to direct the received additional light from the second left lens barrel 604A and second right lens barrel 604B to a second plurality of image sensors of the imaging apparatus 600. For example, the second plurality of image sensors may include and a second left image sensor 622A associated with the second left lens barrel 604A and a second right image sensor 622B associated with the second right lens barrel 604B. Accordingly, the second left dichroic mirror 618A and the second right dichroic mirror 618B may be configured to direct the received additional light to the second left image sensor 622A and the second right image sensor 622B, respectively, along the second parallel left and right optical paths (e.g., along the second left optical path 614A and the second right optical path 614B).

According to aspects, the first plurality of image sensors (e.g., the first left image sensor 620A and the first right image sensor 620B) may be configured to receive the light after passing through the first stereoscopic lens set and being directed by the first left dichroic mirror 616A and the first right dichroic mirror 616B, respectively. Further, each image sensor of the first plurality of image sensors (e.g., the first left image sensor 620A and the first right image sensor 620B) may be configured to generate first image data based on the light received from the first stereoscopic lens set. For example, the first left image sensor 620A may be configured to generate first left image data based on the received light from the first left lens barrel 602A and the first right image sensor 620B may be configured to generate first right image data based on the received light from the first right lens barrel 602B. In some embodiments, the first image data (e.g., first left image data and first right image data) may provide images of a first field-of-view of the target surgical site 603, such as the narrow field-of-view described above showing minute details of the target surgical site 603.

Similarly, the second plurality of image sensors (e.g., the second left image sensor 622A and the second right image sensor 622B) may be configured to receive the additional light after passing through the second stereoscopic lens set and being directed by the second left dichroic mirror 618A and the second right dichroic mirror 618B, respectively. Further, each image sensor of the second plurality of image sensors (e.g., the second left image sensor 622A and the second right image sensor 622B) may be configured to generate second image data based on the additional light received from the second stereoscopic lens set. For example, the second left image sensor 622A may be configured to generate second left image data based on the received additional light from the second left lens barrel 604A and the second right image sensor 622B may be configured to generate second right image data based on the received additional light from the second right lens barrel 604B. In some embodiments, the second image data (e.g., second left image data and second right image data) may provide images of a second field-of-view of the target surgical site 603, such as the "bigger picture" or wide field-of-view of the target surgical site 603, described above.

Figure 7:
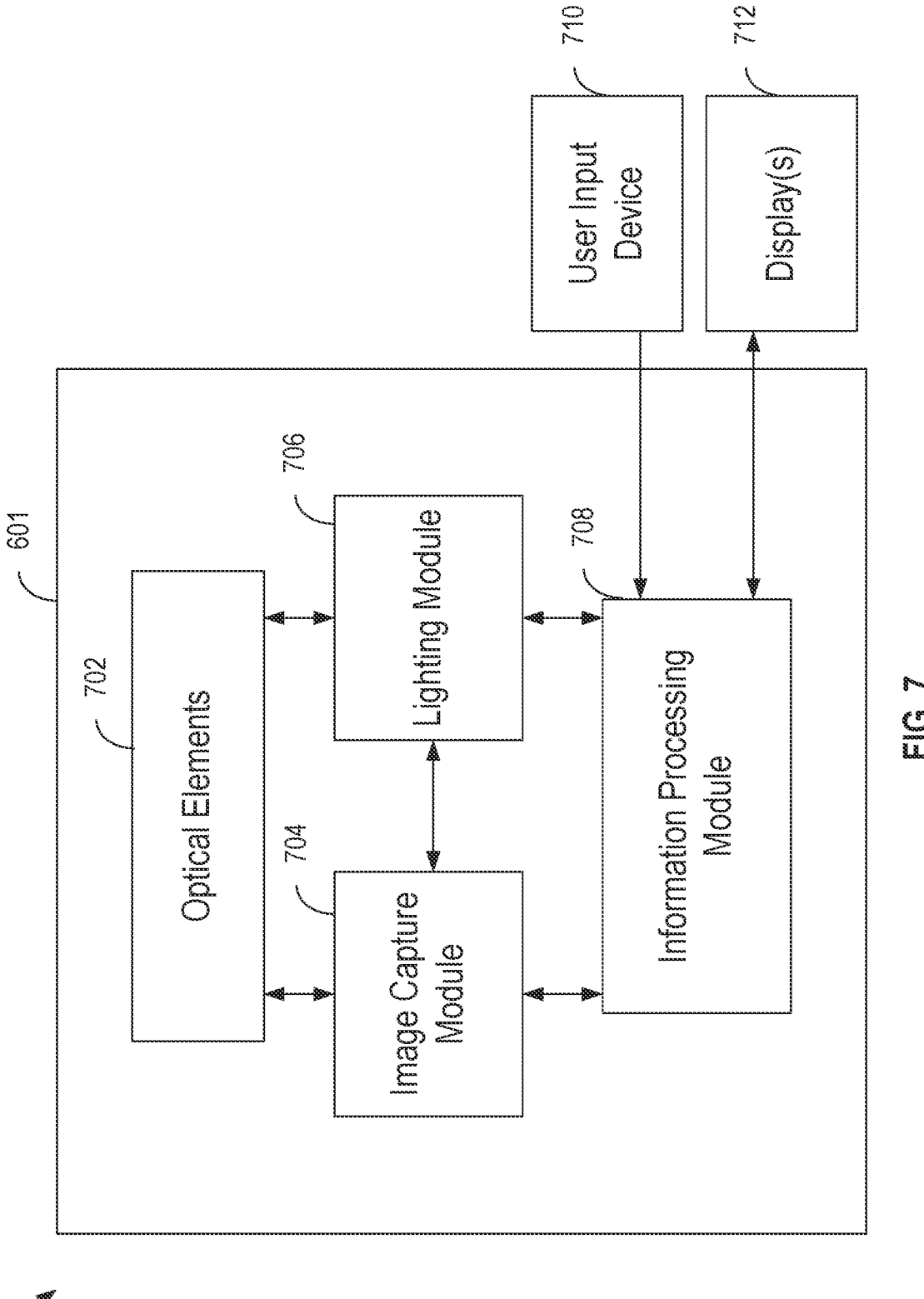
FIG. 7 shows a diagram of modules of the example imaging apparatus for acquiring and processing image data.

As will be explained in greater detail below, the image data from corresponding left and right image sensors may be converted into stereoscopic video data for display on a display monitor by one or more processors of the imaging apparatus 600. For example, FIG. 7 shows a diagram of modules of the example imaging apparatus 600 for acquiring and processing image data, according to an example embodiment of the present disclosure. It should be appreciated that the modules are illustrative of operations, methods, algorithms, routines, and/or steps performed by certain hardware, controllers, processors, drivers, and/or interfaces. In other embodiments, the modules may be combined, further partitioned, and/or removed. Further, one or more of the modules (or portions of a module) may be provided external to the imaging apparatus 600 such as in a remote server, computer, and/or distributed computing environment.

In the illustrated embodiment of FIG. 7, the optical elements 702 may include the first left lens barrel 602A, the first right lens barrel 602B, the second left lens barrel 604A, the second right lens barrel 604B, the first left fixed focal length lens 606A, the first right fixed focal length lens 606B, the second left fixed focal length lens 608A, the second right fixed focal length lens 608B, the light source 610, the first left dichroic mirror 616A, the first right dichroic mirror 616B, the second left dichroic mirror 618A, the second right dichroic mirror 618B, the first left image sensor 620A, the first right image sensor 620B, the second left image sensor 622A, and the second right image sensor 622B. The optical elements 702 (specifically the left and right image sensors 620A, 620B, 622A, and 622B) are communicatively coupled to an image capture module 704 and a motor and lighting module 706. The image capture module 704 is communicatively coupled to an information processing module 708, which may be communicatively coupled to an externally located user input device 710 and one or more display monitors 712. In some embodiments, the one or more display monitors may be examples of the display monitors 512 and/or 514 illustrated in FIG. 5.

The example image capture module 704 is configured to receive image data from the left and right image sensors 620A, 620B, 622A, and 622B. For example, the image capture module 704 may be configured to receive the first left image data from the first left image sensor 620A, the first right image data from the first right image sensor 620B, the second left image data from the second left image sensor 622A, and the second right image data from the second right image sensor 622B. The image capture module 1404 may also specify image recording properties, such as frame rate and exposure time for capturing the image data.

The example lighting module 706 is configured to control the light source 610. For example, in some embodiments, the lighting module 706 may include one or more drivers for controlling the light source 610 to emit light on the target surgical site 603.

The example information processing module 708 is configured to process image data for display. For instance, the information processing module 708 may provide color correction to image data, filter defects from the image data, and/or render image data for stereoscopic display. The information processing module 708 may also perform one or more calibration routines to calibrate the imaging apparatus 600 by providing instructions to the image capture module 704 and/or the motor and lighting module 706 to perform specified adjustments to the optical elements. The information processing module 708 may further determine and provide real-time instructions to the image capture module 704 and/or the motor and lighting module 706 to improve image alignment and/or reduce spurious parallax.

In some embodiments, the information processing module 708 may include one or more processors that are communicatively coupled to the first plurality of image sensors (e.g., the first left image sensor 620A and the first right image sensor 620B) and to the second plurality of image sensors (e.g., the second left image sensor 622A and the second right image sensor 622B). In some embodiments, the one or more processors may be configured to convert the first image data into first stereoscopic video data for display on the one or more display monitors 712. For example, in some embodiments, the one or more processors may be configured to combine the first left image data generated by the first left image sensor 620A with the first right image data generated by the first right image sensor 620B into the first stereoscopic video data. In some embodiments, converting the first image data into first stereoscopic video data may include interleaving rows of pixels of the first left image data and first right image data. In some embodiments, the first stereoscopic video data may represent and show the narrow field-of-view of the target surgical site 603, as discussed above with respect to the first image data.

Additionally, the one or more processors of the information processing module 708 may be configured to convert the second image data into second stereoscopic video data for display on the one or more display monitors 712. For example, in some embodiments, the one or more processors may be configured to combine the second left image data generated by the second left image sensor 622A with the second right image data generated by the second right image sensor 622B into the second stereoscopic video data. In some embodiments, converting the second image data into second stereoscopic video data may include interleaving rows of pixels of the second left image data and second right image data. In some embodiments, the second stereoscopic video data may represent and show the "bigger picture" or wide field-of-view of the target surgical site 603, as discussed above with respect to the second image data.

Figures 8A, 8B:
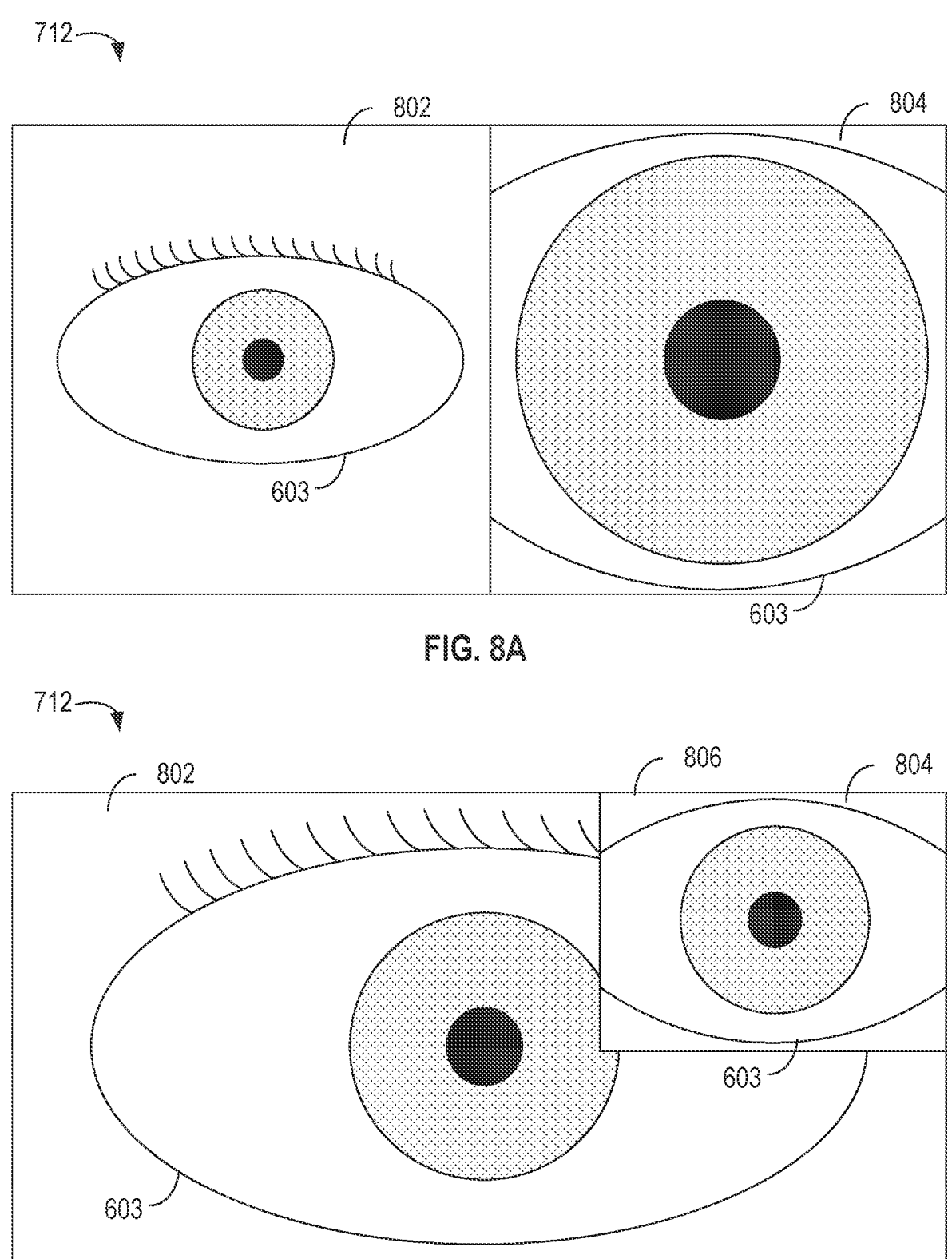
FIG. 8A shows a display configuration for stereoscopic image data.
FIG. 8B show a display configuration for stereoscopic image data.

In some embodiments, the one or more processors of the information processing module 708 may be configured to display only one of the first stereoscopic video data or the second stereoscopic video data at a time on the one or more display monitors 712. In other embodiments, the one or more processors of the information processing module 708 may be configured to display the first stereoscopic video data on the one or more display monitors 712 simultaneously with the second stereoscopic video data. For example, in some embodiments, the one or more processors may display the first stereoscopic video data and the second stereoscopic video data side-by-side on the one or more display monitors 712. An example of this side-by-side display is illustrated in FIG. 8A. For example, as shown in FIG. 8A, the one or more processors may display the first stereoscopic video data 802 (e.g., corresponding to the "bigger picture" or wide field-of-view of the target surgical site 603) next to the second stereoscopic video data 804 (e.g., corresponding to the narrow field-of-view of the target surgical site 603).

In certain embodiments, the one or more processors may display the first stereoscopic video data and the second stereoscopic video data on the one or more display monitors 712 using a picture-in-picture configuration. An example of this picture-in-picture configuration is illustrated in FIG. 8B. For example, as shown in FIG. 8B, the one or more processors may display the first stereoscopic video data 802 (e.g., corresponding to the "bigger picture" or wide field-of-view of the target surgical site 603) spanning the entire display area of the one or more display monitors. Further, the one or more processors may display the second stereoscopic video data 804 (e.g., corresponding to the narrow field-of-view of the target surgical site 603) in a frame within the first stereoscopic video data 802.

The example user input device 710 may include a computer to provide instructions for changing operation of the imaging apparatus 600. The user input device 710 may also include controls for selecting parameters and/or features of the imaging apparatus 600. In some embodiments, the user input device 710 may be configured to allow a user of the imaging apparatus 600 to switch between different magnification levels and fields-of-view of the target surgical site 603. For example, in some embodiments, the user input device 710 may allow a user of the imaging apparatus 600 to switch between the first fixed magnification level associated with fixed focal length lenses 606A and 606B (e.g., the narrow field-of-view of the target surgical site 603) to the second fixed magnification level associated with fixed focal length lenses 608A and 608B (e.g., the "bigger picture"/wide field-of-view of the target surgical site 603).

Because fixed focal length lenses 606A, 606B, 608A, and 608B of the imaging apparatus 600 do not have moving parts, the different fields-of-view of the target surgical site 603 (e.g., the narrow field-of-view in the first stereoscopic video data and the wide field-of-view in the second stereoscopic video data) may be interchanged and displayed on the one or more display monitors 712 almost instantly. Additionally, in some embodiments, the user input device 710 may also be configured to allow the user of the imaging apparatus 600 to switch between different display configurations associated with the first stereoscopic video data and the second stereoscopic video data, such as the side-by-side configuration illustrated in FIG. 8A and the picture-in-picture configuration illustrated in FIG. 8B.

Further, in some embodiments, user input device 710 may include a button or a foot pedal on the imaging apparatus 600 that allows the user to switch between the different magnification levels and/or display configurations. In some embodiments, the user input device 710 may be hardwired to the information processing module 1408. Additionally or alternatively, the user input device 710 is wirelessly or optically communicatively coupled to the information processing module 1408.

While the imaging apparatus 600 is describe above as including a first stereoscopic lens set and a second stereoscopic lens set each associated with a different fixed magnification level, it should be understood that the imaging apparatus may include any number of stereoscopic lens sets (e.g., one, two, three, or more) that are each associated with a different fixed magnification level. Additionally, in some embodiments, the first stereoscopic lens set may include fixed focal length lenses and be associated with a fixed magnification level while the second stereoscopic lens set may include moving zoom lenses (e.g., similar to the front and rear zoom lenses in the a zoom lens assembly 416 of the stereoscopic visualization camera 300) and associated with an adjustable magnification level.

FIG. 9 illustrates an example process 900 for displaying different stereoscopic video data of a target surgical site. In some embodiments, the different stereoscopic video data may be associated with different fields-of-view and magnification levels of the target surgical site. In some embodiments, the process 900 may be performed by an imaging apparatus, such as the imaging apparatus 600, or one or more component in the imaging apparatus 600, such as the optical elements 702, the image capture module 704, the lighting module 706, the information processing module 708, the user input device 710, and/or the one or more display monitors 712.

The process 900 begins at 902 with receiving light from a target surgical site (e.g., target surgical site 603) using a first stereoscopic lens set. The first stereoscopic lens set may include one or more components, such as the first left lens barrel 602A, the first right lens barrel 602B, the first left fixed focal length lens 606A, and/or the first right fixed focal length lens 606B of FIGS. 6A-6C. In some embodiments, the light received from the target surgical site refers to a portion of the light that is reflected from the target surgical site after being emitted from a light source (e.g., light source 610). In some embodiments, the light from the target surgical site may be received by a first plurality of image sensors, such as the first left image sensor 620A and the first right image sensor 620B.

The process 900 continues at 904 with receiving additional light from the target surgical site using a second stereoscopic lens set. The second stereoscopic lens set may include one or more components, such as the second left lens barrel 604A, the second right lens barrel 604B, the second left fixed focal length lens 608A, and/or the second right fixed focal length lens 608B. In some embodiments, the additional light from the target surgical site may be received by a second plurality of image sensors, such as the second left image sensor 622A and the second right image sensor 622B.

The process 900 continues at 906 with generating first image data and second image data based, respectively, on the light received using the first stereoscopic lens set and on the additional light received using the first stereoscopic lens set. For example, in some embodiments, the first plurality of image sensors (e.g., the first left image sensor 620A and the first right image sensor 620B) may be used to generate the first image data based on the light received using the first stereoscopic lens set. Additionally, the second plurality of image sensors (e.g., the second left image sensor 622A and the second right image sensor 622B) may be used to generate the first image data based on the additional light received using the second stereoscopic lens set.

The process 900 continues at 908 with converting the first image data into first stereoscopic video data and the second image data into second stereoscopic video data. In some embodiments, one or more processors of the information processing module 708 may be used to convert the first image data into first stereoscopic video data and the second image data into second stereoscopic video data. In some embodiments, converting the first image data into the first stereoscopic video data may involve interleaving rows of pixels of first left image data generated by the first left image sensor 620A with first right image data generated by the first right image sensor 620B. Similarly, converting the second image data into the second stereoscopic video data may involve interleaving rows of pixels of second left image data generated by the second left image sensor 622A with second right image data generated by the second right image sensor 622B.

The process 900 continues at 910 with displaying the first stereoscopic video data and the second stereoscopic video data on a display monitor, such as the one or more display monitors 712. In some embodiments, displaying the first stereoscopic video data and the second stereoscopic video data on a display monitor may be performed by the one or more processors of the information processing module 708. In some embodiments, displaying the first stereoscopic video data and the second stereoscopic video data may include simultaneously displaying the first stereoscopic video data and the second stereoscopic video data on the display monitor. In some embodiments, simultaneously displaying the first stereoscopic video data and the second stereoscopic video data on the display monitor may include displaying first stereoscopic video data and the second stereoscopic video data using a side-by-side configuration, as illustrated in FIG. 8A. In other embodiments, simultaneously displaying the first stereoscopic video data and the second stereoscopic video data on the display monitor may include simultaneously displaying first stereoscopic video data and the second stereoscopic video data using a picture-in-picture configuration, as illustrated in FIG. 8B.

In some embodiments, the process 900 may further include receiving input from a user and, based on the input from the user, switching from displaying the first stereoscopic video data on the display monitor to displaying the second stereoscopic video data on the display monitor.

Aspects Related to an Imaging Apparatus Including Multiple Stereoscopic Cameras In certain ophthalmic surgeries, being able to view a target surgical site (e.g., associated with a patient's eye), such as the target surgical site 603, from different viewing angles is important. For example, after retinal surgery, surgeons need to look for small retina tears and residual vitreous at a periphery of the eye. Additionally, in cataract surgeries, surgeons may need a different angles of view to see under an edge of the iris of the eye to see if an intraocular lens (IOL) has been placed in a sulcus of a capsular bag of the eye. Another type of surgery in which different viewing angles are important is minimally-invasive glaucoma surgery. In minimally-invasive glaucoma surgery, the surgeon may need different angles of view when removing a trabecular meshwork of the eye (e.g., an area of tissue in the eye located around the base of the cornea) and/or when placing stents around the cornea to allow for proper drainage of fluid within the eye.

These different viewing angles can be achieved using traditional techniques and a surgical microscope that includes a camera positioned directly above the target surgical site. For example, one way of achieving these different viewing angles is through a technique known as scleral depression. Scleral depression involves inserting a tip of a scleral depressor between a globe and an orbit of the eye. A space occupied by the probe displaces the retina inward and creates an elevation. This technique enhances contrast between a retinal lesion and the surrounding retinal tissue allowing for a peripheral view of the retina via the camera positioned directly above. Another way to achieve the different viewing angles is by moving the patient's head slightly. In extreme cases, a headset connected to an indirect ophthalmoscope lens can be used to obtain these different views.

While these traditional techniques may be able to achieve different viewing angle of a target surgical site, these techniques are not ideal and have certain drawbacks. For example, scleral depression can cause trauma to the patient's eye and lead to longer recovery times and additional pain. Additionally, scleral depression is another step in the surgeon's workflow, leading to longer and less efficient surgeries. Moreover, moving the patient's head is also dangerous for the patient and interrupts normal workflow. Additionally, there is no guarantee that the patient's eye will be in the same place after moving the patient's head back, again interrupting workflow and causing alignment issues that require the surgical microscope to be moved.

Newer techniques for achieving different views of the target surgical site involve using a surgical microscope that includes an orbiting camera with lock-to-target functionality. For example, in these types of surgical microscopes, the camera may be positioned above the target surgical site and free to different orbital positions around the target surgical site to obtain the different views of the target surgical site. Additionally, to help facilitate this movement, the lock-to-target functionality allows the camera to lock on to the target surgical site while moving to a new orbital position so that the patient does not have to be repositioned. However, these types of surgical microscopes are expensive and have bulky controller boxes, necessitating a larger cart and bigger operating room footprint. Moreover, when a different view of the target surgical site is needed, the surgeon still needs to wait for the camera of the surgical microscope to move to a new position, which interrupts surgical work flow and results in longer surgeries. Additionally, the parts that facilitate this type of movement are expensive and prone to malfunction, leading to complex and costly repairs as well as loss of use for long periods of time.

Accordingly, aspects of the present disclosure provide an ophthalmic imaging apparatus that includes a plurality of camera heads mounted in different orbital positions above a target surgical site. Each camera head of the plurality of camera heads may be configured to provide a different viewing angle of the target surgical site. For example, in some embodiments, the ophthalmic imaging apparatus may include a first camera head that is located in a first an orbital position above the target surgical. The first orbital position may be directly above the target surgical site and allow the first camera head to provide a first viewing angle of the target surgical site. Additionally, in some embodiments, the ophthalmic imaging apparatus may include at least one additional camera head positioned in an additional orbital position above the target surgical site. In some embodiments, this additional orbital position may be located laterally to the first orbital position and may allow the additional camera to provide a second viewing angle of the target surgical site different from the first viewing angle. In some embodiments, the first viewing angle may provide a frontal view of the target surgical site while the second viewing angle may provide a peripheral view of the target surgical site In some embodiments, these different viewing angles of the target surgical site may be simultaneously displayed to the surgeon on a display monitor. In some embodiments, these different field-of-views may be displayed using a picture-in-picture (PIP) configuration or side by side. In some embodiments these different viewing angles may be individually or sequentially displayed to the surgeon on the display monitor. In such embodiments, the surgeon may be able to switch between the different viewing angles almost instantly at the push of a button.

By providing multiple camera heads associated with different viewing angles of the target surgical site and displaying different fields-of-view of the target surgical site corresponding to these different viewing angles (e.g., simultaneously or individually but instantly switchable via a push of a button), the surgeon does not need to pause surgery to move a patient's head to obtain a peripheral view of the target surgical site or correct alignment issues when moving the patient's head back. Nor does the surgeon need to perform scleral depression, eliminating the potential additional trauma to the patient associated with scleral depression.

Moreover, because these different viewing angles are provided by multiple camera heads mounted in different orbital positions above the target surgical site, the surgeon may not need to pause surgery to wait for a single camera head of certain surgical microscopes to lock on to a target and physically move to a new position to obtain a different view of the target surgical site. Further, providing multiple camera heads mounted in different orbital positions above the target surgical site eliminates the need for the parts that facilitate the physical movement of the single camera of these certain surgical microscopes, avoiding the manufacturing expense as well as the complex and costly repairs of such moving parts.

Figure 10:
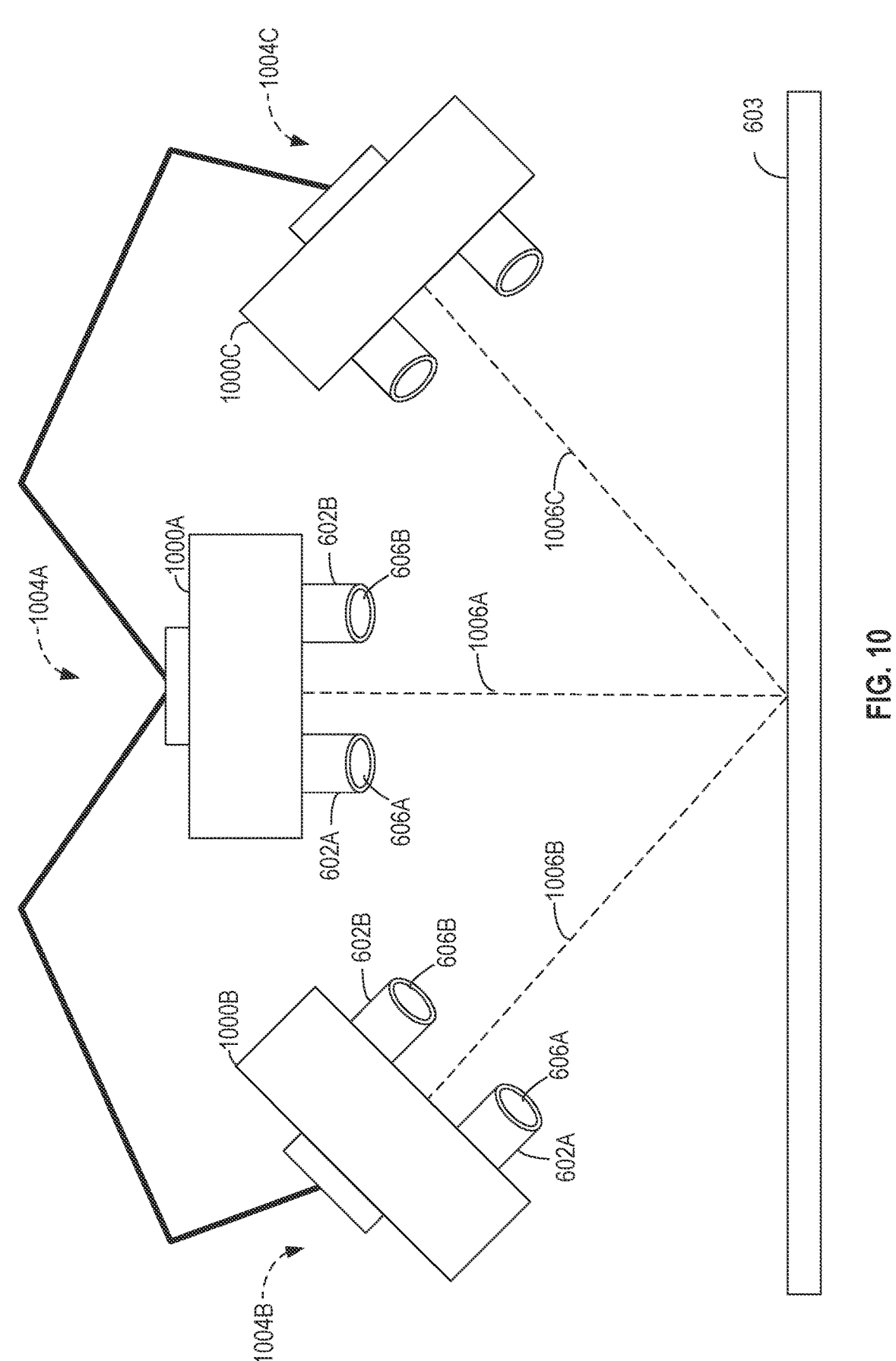
FIG. 10 illustrates an ophthalmic imaging apparatus that includes a plurality of camera heads, each providing a different viewing angle of a target surgical site.

FIG. 10 illustrates a frontal view of an ophthalmic imaging apparatus 1000 that includes a plurality of camera heads, each providing a different viewing angle of a target surgical site, such as the target surgical site 603. In some embodiments, the ophthalmic imaging apparatus 1000 may be implemented in a microsurgical environment, such as the microsurgical environment 500. More specifically, in some embodiments, the ophthalmic imaging apparatus 1000 is configured to replace the stereoscopic visualization camera 300 in the microsurgical environment 500.

In some embodiments, as illustrated, the ophthalmic imaging apparatus 1000 includes a first camera head 1002A, a second camera head 1002B, and a third camera head 1002C. Each of the first camera head 1002A, a second camera head 1002B, and a third camera head 1002C may be an example of the imaging apparatus 600 illustrated in FIGS. 6A, 6B, and 6C. Thus, in addition to providing different viewing angles of the target surgical site 603, each of the first camera head 1002A, a second camera head 1002B, and a third camera head 1002C may also be capable of providing multiple different fixed magnification levels (e.g., via different fixed focal length lenses) that, in turn, provide different fields-of-view of the target surgical site 603, such as the narrow field-of-view and wide/"bigger picture" field-of-view described above. The frontal view shown in FIG. 10 is from the perspective of viewing the front side illustrated in FIG. 6A directly head-on.

In some embodiments, the first camera head 1002A includes at least a one stereoscopic lens set, which is configured to receive light from the target surgical site 603 and provide a first viewing angle 1006A of the target surgical site 603. In some embodiments, the second camera head 1002B includes at least one other stereoscopic lens set, which is configured to receive light from the target surgical site 603 and provide a second viewing angle 1006B of the target surgical site 603. In some embodiments, the at least one stereoscopic lens set includes a first stereoscopic lens set and a second stereoscopic lens set. In some embodiments, the at least one other stereoscopic lens set includes a third stereoscopic lens set and a fourth stereoscopic lens set.

In some embodiments, the first stereoscopic lens set comprises at least a first left lens barrel (e.g., the first left lens barrel 602A) and a first right lens barrel (e.g., the first right lens barrel 602B) defining respective first parallel left and right optical paths Additionally, in some embodiments, each of the first left lens barrel and the first right lens barrel includes a first fixed focal length lens (e.g., first left fixed focal length lens 606A and first right fixed focal length lens 606B) configured to magnify the received light according to a first fixed magnification level.

In some embodiments, the second stereoscopic lens set comprises at least a second left lens barrel (e.g., the second left lens barrel 604A) and a second right lens barrel (e.g., the second right lens barrel 604B) defining respective second parallel left and right optical paths. Additionally, in some embodiments, each of the second left lens barrel and the second right lens barrel includes a second fixed focal length lens (e.g., second left fixed focal length lens 608A and second right fixed focal length lens 608B) configured to magnify the received additional light according to a second fixed magnification level different from the first fixed magnification level.

In some embodiments, the first camera head 1002A further includes a first plurality of image sensors configured to receive the light after passing through the first stereoscopic lens set. The first plurality of image sensors comprises a first left image sensor (e.g., first left image sensor 620A) configured to generate first left image data based on the light received from the first stereoscopic lens set. In some embodiments, the first left image data may include image data of the target surgical site 603 from the perspective of the first viewing angle 1006A. In some embodiments, the first left image sensor is configured to receive the light from the first left lens barrel. The first plurality of image sensors also comprises a first right image sensor (e.g., first right image sensor 620B) configured to generate first right image data based on the light received from the first stereoscopic lens set. In some embodiments, the first right image data may include image data of the target surgical site 603 from the perspective of the first viewing angle 1006A. In some embodiments, the first right image sensor is configured to receive the light from the first right lens barrel.

Additionally, the first camera head 1002A includes a second plurality of image sensors configured to receive the light after passing through the second stereoscopic lens set. The second plurality of image sensors comprises a second left image sensor (e.g., second left image sensor 622A) configured to generate second left image data based on the light received from the second stereoscopic lens set. In some embodiments, the second left image sensor is configured to receive the light from the second left lens barrel. Additionally, the second plurality of image sensors comprises a second right image sensor (e.g., second right image sensor 622B) configured to generate second right image data based on the light received from second stereoscopic lens set. In some embodiments, the second right image sensor is configured to receive the light from the second right lens barrel.

Additionally, the first camera head 1002A includes a first processor (e.g., information processing module 708) communicatively coupled to the first plurality of image sensors and the second plurality of image sensors. The first processor is configured to convert the first left image data and the first right image data into first stereoscopic video data for display on a display monitor (e.g., display monitor 712). Additionally, the first processor is configured convert the second left image data and second right image data into second stereoscopic video data for display on the display monitor. In some embodiments, the first stereoscopic video data and the second stereoscopic video data may include video data of the target surgical site 603 from the perspective of the first viewing angle 1006A.

As noted above, in some embodiments, the at least one other stereoscopic lens set of the second camera head 1002B includes the third stereoscopic lens set and the fourth stereoscopic lens set.

In some embodiments, the third stereoscopic lens set comprises at least a third left lens barrel (e.g., the first left lens barrel 602A) and a third right lens barrel (e.g., the first right lens barrel 602B) defining respective third parallel left and right optical paths. Additionally, in some embodiments, each of the third left lens barrel and the third right lens barrel includes a third fixed focal length lens (e.g., first left fixed focal length lens 606A and first right fixed focal length lens 606B) configured to magnify the received light according to the first fixed magnification level.

In some embodiments, the second stereoscopic lens set comprises at least a fourth left lens barrel (e.g., the second left lens barrel 604A) and a fourth right lens barrel (e.g., the second right lens barrel 604B) defining respective fourth parallel left and right optical paths. Additionally, in some embodiments, each of the fourth left lens barrel and the second right lens barrel includes a fourth fixed focal length lens (e.g., second left fixed focal length lens 608A and second right fixed focal length lens 608B) configured to magnify the received additional light according to the second fixed magnification level different from the first fixed magnification level.

In some embodiments, the second camera head 1002B further includes a third plurality of image sensors configured to receive the light after passing through the third stereoscopic lens set. The third plurality of image sensors comprises a third left image sensor (e.g., first left image sensor 620A) configured to generate third left image data based on the light received from the third stereoscopic lens set. In some embodiments, the third left image data may include image data of the target surgical site 603 from the perspective of the second viewing angle 1006B. In some embodiments, the third left image sensor is configured to receive the light from the third left lens barrel. The third plurality of image sensors also comprises a third right image sensor (e.g., first right image sensor 620B) configured to generate third right image data based on the light received from the third stereoscopic lens set. In some embodiments, the fourth left image data may include image data of the target surgical site 603 from the perspective of the second viewing angle 1006B. In some embodiments, the third right image sensor is configured to receive the light from the third right lens barrel.

Additionally, the second camera head 1002B includes a fourth plurality of image sensors configured to receive the light after passing through the fourth stereoscopic lens set. The fourth plurality of image sensors comprises a fourth left image sensor (e.g., second left image sensor 622A) configured to generate fourth left image data based on the light received from the fourth stereoscopic lens set. In some embodiments, the fourth left image sensor is configured to receive the light from the fourth left lens barrel. Additionally, the fourth plurality of image sensors comprises a fourth right image sensor (e.g., second right image sensor 622B) configured to generate fourth right image data based on the light received from fourth stereoscopic lens set. In some embodiments, the fourth right image sensor is configured to receive the light from the fourth right lens barrel.

Additionally, the second camera head 1002B includes a second processor (e.g., information processing module 708) communicatively coupled to the third plurality of image sensors and the fourth plurality of image sensors. The second processor is configured to convert the third left image data and the third right image data into third stereoscopic video data for display on a display monitor (e.g., display monitor 712). Additionally, the second processor is configured convert the fourth left image data and fourth right image data into fourth stereoscopic video data for display on the display monitor. In some embodiments, the third stereoscopic video data and the fourth stereoscopic video data may include video data of the target surgical site 603 from the perspective of the second viewing angle 1006B.

Because the third camera head 1002C may be the same as the first camera head 1002A and the second camera head 1002B, the discussion regarding the optical elements (e.g., lens barrels, fixed focal length lenses, etc.) and signal processing elements (e.g., processors, image sensors, etc.) have been omitted here. Additionally, because the first camera head 1002A, the second camera head 1002B, and the third camera head 1002C are all examples of the imaging apparatus 600 shown in FIGS. 6A, 6B, and 6C, additional details regarding the optical elements and signal processing elements of these camera heads may be found in the description of the imaging apparatus 600 above.

In some embodiments, however, the first camera head 1002A, the second camera head 1002B, and the third camera head 1002C may each be a different type of camera head while still providing different viewing angles of the target surgical site (e.g., viewing angles 1006A-1006C). For example, in some embodiments, the first camera head 1002A may be an example of the imaging apparatus 600 illustrated in FIGS. 6A, 6B, and 6B including multiple stereoscopic lens sets (e.g., the first stereoscopic lens set and the second stereoscopic lens set) each associated with a different fixed magnification level. In some embodiments, the second camera head 1002B may be similar to the imaging apparatus 600 illustrated in FIGS. 6A, 6B, and 6B but only include one stereoscopic lens set (e.g., the first stereoscopic lens set associated with a fixed magnification level. Further, in some embodiments, the third camera head 1002C may be an example of the stereoscopic visualization camera 300 illustrated in FIGS. 3-4, which includes moving front and rear zoom lenses in the zoom lens assembly 416 to achieve different magnification levels.

As shown, the first camera head 1002A is mounted in a first orbital position 1004A directly above the target surgical site 603. The second camera head 1002B is mounted in a second orbital position 1004B above the target surgical site 603 laterally, to the left of the first orbital position 1004A of the first camera head 1002A. Additionally, the third camera head 1002C is mounted in a third orbital position 1004C above the target surgical site 603 laterally, to the right of the first orbital position 1004A of the first camera head 1002A.

As shown, the first orbital position 1004A of the first camera head 1002A provides a first viewing angle 1006A of the target surgical site 603. The second orbital position 1004B of the second camera head 1002B provides a second viewing angle 1006B of the target surgical site 603, which is different from the first viewing angle 1006A. Further, the third orbital position 1004C of the third camera head 1002C provides a third viewing angle 1006C of the target surgical site 603, which is different from the first viewing angle 1006A and the second viewing angle 1006B.

The first viewing angle associated with the first camera head 1002A provides a frontal view of the target surgical site, while the second viewing angle associated with the second camera head 1002B provides a first peripheral view of the target surgical site 603. Similarly, the third viewing angle associated with the third camera head 1002C provides a second peripheral view of the target surgical site 603. Accordingly, by including multiple cameras heads (e.g., the first camera head 1002A, the second camera head 1002B, and the third camera head 1002C), the ophthalmic imaging apparatus 1000 is able to provide different views of the target surgical site 603, which is especially helpful during certain types of ophthalmic procedures.

For example, as noted above, during retinal surgery, surgeons need to look for small retina tears and residual vitreous at a periphery of a patient's eye. One way to accomplish this is by scleral depression, which involves inserting a tip of a scleral depressor between a globe and an orbit of the eye, displacing the retina inward and creating an elevation to be able to see the periphery of the eye. As noted, scleral depression is not ideal and can cause additional trauma to the patient.

The ophthalmic imaging apparatus 1000 helps to avoid the need for scleral depression. For example, during retinal surgery, not only is the surgeon able to see a frontal view of the patient's eye via the first viewing angle of the first camera head 1002A, but the surgeon may also switch between the different viewing angles provided by the second camera head 100BA and/or the third camera head 1002C to see peripheral views of the patient's eye in order to determine whether there is any small retina tears or residual vitreous.

In some embodiments, in addition to being able to display and switch between different magnification levels and fields-of-view of the target surgical site 603, as described above, the ophthalmic imaging apparatus 1000 may allow the surgeon to be able to display and switch between video data associated with the different viewing angles of the target surgical site 603. As the first camera head 1002A, the second camera head 1002B, and the third camera head 1002C are examples of the imaging apparatus 600, the following description regarding displaying and switching between video data associated with the different viewing angles will be made in relation to FIG. 7, which shows the different modules the imaging apparatus 600 for acquiring and processing image data.

For example, in some embodiments, the one or more processors of the information processing module illustrated in FIG. 7 may be configured to display only the stereoscopic video data associated with the first viewing angle 1006A (e.g., the first stereoscopic video data and/or the second stereoscopic video data) on the one or more display monitors 712. In some embodiments, the information processing module 708 illustrated in FIG. 7 may be configured to display only the stereoscopic video data associated with the second viewing angle 1006B (e.g., the third stereoscopic video data and/or the fourth stereoscopic video data) on the one or more display monitors 712.

In some embodiments, the one or more processors of the information processing module 708 may be configured to display the stereoscopic video data associated with the first viewing angle 1006A (e.g., the first stereoscopic video data and/or the second stereoscopic video data) simultaneously with stereoscopic video data associated with the second viewing angle 1006B (e.g., the third stereoscopic video data and/or the fourth stereoscopic video data) on the one or more display monitors 712. For example, in some cases, the one or more processors of the information processing module 708 may display the first stereoscopic video data associated with the first viewing angle 1006A simultaneously with the third stereoscopic video data associated with the second viewing angle 1006B. In general, the one or more processors of the information processing module 708 may be configured to different combinations of the first stereoscopic video data, second stereoscopic video data, third stereoscopic video data, and fourth stereoscopic video data on the one or more display monitors 712. In some cases, the one or more processors of the information processing module 708 may display the stereoscopic video data associated with these different viewing angles using a side-by-side configuration (e.g., similar to that illustrated in FIG. 8A) or a picture-in-picture configuration (e.g., similar to that illustrated in FIG. 8B).

FIG. 11 illustrates an example process 1100 for displaying stereoscopic video data of a target surgical site. In some embodiments, the different stereoscopic video data may be associated with different viewing angles of the target surgical site. In some embodiments, the process 1100 may be performed by an imaging apparatus, such as the ophthalmic imaging apparatus 1000 illustrated in FIG. 10, including multiple camera heads (e.g., two or more of the first camera head 1002A, the second camera head 1002B, or the third camera head 1002C). In some cases, the process 1100 may be performed by one or more components of any of these camera heads, such as the optical elements 702, the image capture module 704, the lighting module 706, the information processing module 708, the user input device 710, and/or the one or more display monitors 712 illustrated in FIG. 7.

The process 1100 begins at 1102 with receiving light from a target surgical site (e.g., target surgical site 603) associated with an eye of a patient using at least one stereoscopic lens set of a first camera head (e.g., first camera head 1002A). In some embodiments, the first camera head is mounted in a first orbital position (e.g., first orbital position 1004A) above the target surgical site. Additionally, in some embodiments, the at least one stereoscopic lens set provides a first viewing angle (e.g., first viewing angle 1006A) of the target surgical site. In some embodiments, the at least one stereoscopic lens set includes a first stereoscopic lens set and a second stereoscopic lens set.

In some embodiments the first stereoscopic lens set may include one or more components, such as the first left lens barrel 602A, the first right lens barrel 602B, the first left fixed focal length lens 606A, and/or the first right fixed focal length lens 606B of FIGS. 6A-6C. Additionally, in some embodiments the second stereoscopic lens set may include one or more components, such as the second left lens barrel 604A, the second right lens barrel 604B, the second left fixed focal length lens 608A, and/or the second right fixed focal length lens 608B.

In some embodiments, the light received from the target surgical site refers to a portion of the light that is reflected from the target surgical site after being emitted from a light source (e.g., light source 610). In some embodiments, the light from the target surgical site may be received by a first plurality of image sensors and second plurality of image sensors, such as the first left image sensor 620A, the first right image sensor 620B, the second left image sensor 622A, and the second right image sensor 622B.

The process continues at 1104 with receiving the light from the target surgical site using at least one other stereoscopic lens set of a second camera head (e.g., the second camera head 1002B). In some embodiments, the second camera head is mounted in a second orbital position (e.g., second orbital position 1004B) above the target surgical site different from the first orbital position. In some embodiments, the at least one other stereoscopic lens set provides a second viewing angle (e.g., second viewing angle 1006B) of the target surgical site different from the first viewing angle of the target surgical site. In some embodiments, the at least one other stereoscopic lens set includes a third stereoscopic lens set and a fourth stereoscopic lens set.

In some embodiments, the third stereoscopic lens set may include one or more components, such as the first left lens barrel 602A, the first right lens barrel 602B, the first left fixed focal length lens 606A, and/or the first right fixed focal length lens 606B of FIGS. 6A-6C. Additionally, in some embodiments, the fourth stereoscopic lens set may include one or more components, such as the second left lens barrel 604A, the second right lens barrel 604B, the second left fixed focal length lens 608A, and/or the second right fixed focal length lens 608B.

The process 1100 continues at 1106 with generating image data based on the light received using the at least one stereoscopic lens set. In some embodiments, generating the image data based on the light received using the at least one stereoscopic lens set comprises generating first image data and second image data based, respectively, on the light received using the first stereoscopic lens set and on the light received using the second stereoscopic lens set. For example, in some embodiments, the first plurality of image sensors (e.g., the first left image sensor 620A and the first right image sensor 620B) may be used to generate the first image data by generating first left image data and first right image data based on the light received using the first stereoscopic lens set. Additionally, the second plurality of image sensors (e.g., the second left image sensor 622A and the second right image sensor 622B) may be used to generate the second image data by generating second left image data and second left image data based on the light received using the second stereoscopic lens set.

The process 1100 continues at 1108 with generating additional image data based on the light received using the at least one other stereoscopic lens set. In some embodiments, generating the additional image data based on the light received using the at least one other stereoscopic lens set comprises generating third image data and fourth image data based, respectively, on the light received using the third stereoscopic lens set and on the light received using the fourth stereoscopic lens set. For example, in some embodiments, the third plurality of image sensors (e.g., the first left image sensor 620A and the first right image sensor 620B) may be used to generate the third image data by generating third left image data and third right image data based on the light received using the third stereoscopic lens set. Additionally, the fourth plurality of image sensors (e.g., the second left image sensor 622A and the second right image sensor 622B) may be used to generate the fourth image data by generating fourth left image data and fourth left image data based on the light received using the fourth stereoscopic lens set.

The process 1100 continues at 1110 with converting the image data into stereoscopic video data and the additional image data into additional stereoscopic video data. For example, in some embodiments, converting the image data into stereoscopic video and the additional image data into additional stereoscopic video data comprises converting the first image data into first stereoscopic video data, the second image data into second stereoscopic video data, the third image data into third stereoscopic video data, and the fourth image data into fourth stereoscopic video data In some embodiments, converting the first image data into the first stereoscopic video data may involve interleaving rows of pixels of the first left image data generated by the first left image sensor with the first right image data generated by the first right image sensor. Similarly, converting the second image data into the second stereoscopic video data may involve interleaving rows of pixels of the second left image data generated by the second left image sensor with the second right image data generated by the second right image sensor. Further, converting the third image data into the third stereoscopic video data may involve interleaving rows of pixels of the third left image data generated by the third left image sensor with the third right image data generated by the third right image sensor. Similarly, converting the fourth image data into the fourth stereoscopic video data may involve interleaving rows of pixels of the fourth left image data generated by the fourth left image sensor with the fourth right image data generated by the fourth right image sensor.

The process 1100 continues at 1112 with displaying at least one of the stereoscopic video data or the additional stereoscopic video data on a display monitor, such as the one or more display monitors 712. In some embodiments, displaying at least one of the stereoscopic video data or the additional stereoscopic video data comprises displaying at least two of the first stereoscopic video data, the second stereoscopic video data, the third stereoscopic video data, or the fourth stereoscopic video data on a display monitor. In some embodiments, displaying the at least two of the first stereoscopic video data, the second stereoscopic video data, the third stereoscopic video data, or the fourth stereoscopic video data on a display monitor may be performed by the one or more processors of the information processing module 708. In some embodiments, displaying the at least two of the first stereoscopic video data, the second stereoscopic video data, the third stereoscopic video data, or the fourth stereoscopic video data may include simultaneously displaying the first stereoscopic video data and the second stereoscopic video data on the display monitor. In some embodiments, simultaneously displaying the first stereoscopic video data and the second stereoscopic video data on the display monitor may include displaying first stereoscopic video data and the second stereoscopic video data using a side-by-side configuration or using a picture-in-picture configuration.

In some embodiments, the process 1100 may further include receiving input from a user and, based on the input from the user, switching from displaying the first stereoscopic video data associated with the first viewing angle on the display monitor to displaying the third stereoscopic video data associated with the second viewing angle on the display monitor.

ADDITIONAL CONSIDERATIONS

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed:

1. An ophthalmic imaging apparatus, comprising:
a first camera head mounted in a first orbital position above a target surgical site associated with an eye of a patient, wherein the first camera head includes at least one stereoscopic lens set providing a first viewing angle of the target surgical site; and
at least a second camera head mounted in a second orbital position above the target surgical site, wherein the second camera head includes at least one other stereoscopic lens set providing a second viewing angle of the target surgical site different from the first viewing angle of the target surgical site;
wherein:
the at least one stereoscopic lens set of the first camera head comprises a first stereoscopic lens set and a second stereoscopic lens set;

the first stereoscopic lens set and the second stereo-
scopic lens set of the first camera head are configured
to receive light from the target surgical site;
the first camera head further includes:
  a first plurality of image sensors configured to
    receive the light after passing through the first
    stereoscopic lens set, wherein the first plurality of
    image sensors comprises:
    a first left image sensor configured to generate first
      left image data based on the light received from
      the first stereoscopic lens set; and
    a first right image sensor configured to generate
      first right image data based on the light received
      from the first stereoscopic lens set;
  a second plurality of image sensors configured to
    receive the light after passing through the second
    stereoscopic lens set, wherein the second plurality
    of image sensors comprises:
    a second left image sensor configured to generate
      second left image data based on the light
      received from the second stereoscopic lens set;
      and
    a second right image sensor configured to generate
      second right image data based on the light
      received from second stereoscopic lens set; and
  a first processor communicatively coupled to the first
    plurality of image sensors and the second plurality
    of image sensors, wherein the first processor is
    configured to:
    convert the first left image data and the first right
      image data into first stereoscopic video data for
      display on a display monitor; and
    convert the second left image data and second
      right image data into second stereoscopic video
      data for display on the display monitor.

2. The ophthalmic imaging apparatus of claim 1, wherein:
the first viewing angle provides a frontal view of the target
  surgical site, and
the second viewing angle provides a peripheral view of
  the target surgical site.

3. The ophthalmic imaging apparatus of claim 1, wherein:
the at least one other stereoscopic lens set of the second
  camera head comprises a third stereoscopic lens set and
  a fourth stereoscopic lens set;
the third stereoscopic lens set and the fourth stereoscopic
  lens set of the second camera head are configured to
  receive light from the target surgical site, and
the second camera head further includes:
  a third plurality of image sensors configured to receive
    the light after passing through the third stereoscopic
    lens set, wherein the third plurality of image sensors
    comprises:
    a third left image sensor configured to generate third
      left image data based on the light received from
      the third stereoscopic lens set, and
    a third right image sensor configured to generate
      third right image data based on the light received
      from the third stereoscopic lens set;
  a fourth plurality of image sensors configured to
    receive the light after passing through the fourth
    stereoscopic lens set, wherein the fourth plurality of
    image sensors comprises:
    a fourth left image sensor configured to generate
      fourth left image data based on the light received
      from the fourth stereoscopic lens set, and a fourth right image sensor configured to generate
      fourth right image data based on the light received
      from fourth stereoscopic lens set; and
  a second processor communicatively coupled to the
    third plurality of image sensors and the fourth plu-
    rality of image sensors, wherein the second proces-
    sor is configured to:
    convert the third left image data and the third right
      image data into third stereoscopic video data for
      display on a display monitor, and
    convert the fourth left image data and fourth right
      image data into fourth stereoscopic video data for
      display on the display monitor.

4. The ophthalmic imaging apparatus of claim 3, wherein
the first stereoscopic lens set of the first camera head and the
third stereoscopic lens set of the second camera head each
individually include at least a first fixed focal length lens
configured to magnify the received light according to a first
fixed magnification level.

5. The ophthalmic imaging apparatus of claim 4, wherein
the second stereoscopic lens set of the first camera head and
the fourth stereoscopic lens set of the second camera head
each individually include at least a second fixed focal length
lens configured to magnify the received light according to a
second fixed magnification level different from the first fixed
magnification level.

6. The ophthalmic imaging apparatus of claim 3, wherein
the first processor is further configured to display the first
stereoscopic video data on the display monitor simultane-
ously with the second stereoscopic video data.

7. The ophthalmic imaging apparatus of claim 3, wherein
the second processor is configured to display the third
stereoscopic video data on the display monitor simultane-
ously with the fourth stereoscopic video data.

8. The ophthalmic imaging apparatus of claim 3, wherein
the first processor and second processor are configured to
display different combinations of the first stereoscopic video
data, second stereoscopic video data, third stereoscopic
video data, and fourth stereoscopic video data on the display
monitor.

9. The ophthalmic imaging apparatus of claim 3, wherein:
the first stereoscopic lens set comprises at least a first left
  lens barrel and a first right lens barrel defining respec-
  tive first parallel left and right optical paths,
each of the first left lens barrel and the first right lens
  barrel includes a first fixed focal length lens configured
  to magnify the received light according to a first
  magnification level,
the first left image sensor is configured to receive the light
  from the first left lens barrel, and
the first right image sensor is configured to receive the
  light from the first right lens barrel
the second stereoscopic lens set comprises at least a
  second left lens barrel and a second right lens barrel
  defining respective second parallel left and right optical
  paths,
each of the second left lens barrel and the second right
  lens barrel includes a second fixed focal length lens
  configured to magnify the received light according to a
  second magnification level different from the first mag-
  nification level,
the second left image sensor is configured to receive the
  light from the second left lens barrel, and
the second right image sensor is configured to receive the
  light from the second right lens barrel.

10. The ophthalmic imaging apparatus of claim 9,
wherein:

the third stereoscopic lens set comprises at least a third left lens barrel and a third right lens barrel defining respective third parallel left and right optical paths, each of the third left lens barrel and the third right lens barrel includes a third fixed focal length lens configured to magnify the received light according to the first magnification level, the third left image sensor is configured to receive the light from the third left lens barrel, the third right image sensor is configured to receive the light from the third right lens barrel, the fourth stereoscopic lens set comprises at least a fourth left lens barrel and a fourth right lens barrel defining respective fourth parallel left and right optical paths, each of the fourth left lens barrel and the fourth right lens barrel includes a fourth fixed focal length lens configured to magnify the received light according to the second magnification level different from the first magnification level, the fourth left image sensor is configured to receive the light from the fourth left lens barrel, and the fourth right image sensor is configured to receive the light from the fourth right lens barrel.

11. A method for stereoscopic video data of a target surgical site using an ophthalmic imaging apparatus, comprising:

receiving light from a target surgical site associated with an eye of a patient using at least one stereoscopic lens set of a first camera head, wherein:

the first camera head is mounted in a first orbital position above the target surgical site, and the at least one stereoscopic lens set provides a first viewing angle of the target surgical site;

receiving the light from the target surgical site using at least one other stereoscopic lens set of a second camera head, wherein:

the second camera head is mounted in a second orbital position above the target surgical site different from the first orbital position, and the at least one other stereoscopic lens set provides a second viewing angle of the target surgical site different from the first viewing angle of the target surgical site;

generating image data based on the light received using the at least one stereoscopic lens set;

generating additional image data based on the light received using the at least one other stereoscopic lens set;

converting the image data into stereoscopic video data and the additional image data into additional stereoscopic video data; and displaying at least one of the stereoscopic video data or the additional stereoscopic video data on a display monitor;

wherein:

the at least one stereoscopic lens set comprises a first stereoscopic lens set and a second stereoscopic lens set;

generating the image data based on the light received using the at least one stereoscopic lens set comprises generating first image data and second image data based, respectively, on the light received using the first stereoscopic lens set and on the light received using the second stereoscopic lens set;

converting the image data into stereoscopic video and the additional image data into additional stereoscopic video data comprises converting the first image data into first stereoscopic video data, the second image data into second stereoscopic video data; and displaying at least one of the stereoscopic video data or the additional stereoscopic video data comprises displaying the first stereoscopic video data and the second stereoscopic video data on the display monitor.

12. The method of claim 11, wherein:

the at least one other stereoscopic lens set comprises a third stereoscopic lens set and a fourth stereoscopic lens set, generating the additional image data based on the light received using the at least one other stereoscopic lens set comprises generating third image data and fourth image data based, respectively, on the light received using the third stereoscopic lens set and on the light received using the fourth stereoscopic lens set, converting the image data into stereoscopic video and the additional image data into additional stereoscopic video data further comprises converting the third image data into third stereoscopic video data, and the fourth image data into fourth stereoscopic video data, and displaying at least one of the stereoscopic video data or the additional stereoscopic video data comprises displaying the third stereoscopic video data and the fourth stereoscopic video data on the display monitor.

13. The method of claim 12, wherein:

the first viewing angle provides a frontal view of the target surgical site, and the second viewing angle provides a peripheral view of the target surgical site.

14. The method of claim 12, wherein:

the first stereoscopic lens set of the first camera head and the third stereoscopic lens set of the second camera head each individually include at least a first fixed focal length lens configured to magnify the received light according to a first fixed magnification level, and the second stereoscopic lens set of the first camera head and the fourth stereoscopic lens set of the second camera head each individually include at least a second fixed focal length lens configured to magnify the received light according to a second fixed magnification level different from the first fixed magnification level.

15. The method of claim 12, further comprising:

receiving input from a user; and based on the input from the user, switching from displaying the first stereoscopic video data on the display monitor to displaying the third stereoscopic video data on the display monitor.

* * * * *